(12) United States Patent
Robinson

(10) Patent No.: US 8,323,194 B2
(45) Date of Patent: Dec. 4, 2012

(54) DETECTION OF BUBBLES DURING HEMODYNAMIC MONITORING WHEN PERFORMING AUTOMATED MEASUREMENT OF BLOOD CONSTITUENTS

(75) Inventor: Mark Ries Robinson, Albuquerque, NM (US)

(73) Assignee: InLight Solutions, Inc., Albuquerque, NM (US)

(*) Notice: Subject to any disclaimer, the term of this patent is extended or adjusted under 35 U.S.C. 154(b) by 431 days.

(21) Appl. No.: 12/641,411

(22) Filed: Dec. 18, 2009

(65) Prior Publication Data

US 2011/0152642 A1    Jun. 23, 2011

(51) Int. Cl.
*A61B 5/00* (2006.01)

(52) U.S. Cl. ..................................................... 600/309

(58) Field of Classification Search ................... 600/309
See application file for complete search history.

(56) References Cited

U.S. PATENT DOCUMENTS

| | | |
|---|---|---|
| 3,812,482 A | 5/1974 | Clark |
| 4,055,175 A | 10/1977 | Clemens et al. |
| 4,151,845 A | 5/1979 | Clemens |
| 4,253,456 A | 3/1981 | Schindler et al. |
| 4,526,569 A | 7/1985 | Bernardi |
| 4,657,529 A | 4/1987 | Prince et al. |
| 4,777,953 A | 10/1988 | Ash et al. |
| 4,805,624 A | 2/1989 | Yao et al. |
| 4,846,548 A | 7/1989 | Klainer |
| 5,002,054 A | 3/1991 | Ash et al. |
| 5,088,978 A | 2/1992 | Hillman et al. |
| 5,089,421 A | 2/1992 | Dieffenbach |
| 5,165,406 A | 11/1992 | Wong |
| 5,176,632 A | 1/1993 | Bernardi |
| 5,288,646 A | 2/1994 | Lundsgaard et al. |
| 5,366,903 A | 11/1994 | Lundsgaard et al. |
| 5,383,848 A | 1/1995 | Hillman et al. |
| 5,487,384 A | 1/1996 | Lee |
| 5,536,237 A | 7/1996 | Prince et al. |
| 5,544,651 A | 8/1996 | Wilk |

(Continued)

FOREIGN PATENT DOCUMENTS

WO    PCT/US91/02911    10/1991

(Continued)

OTHER PUBLICATIONS

AAMI TIR No. 9, © 2000, "Evaluation of Clinical Systems for Invasive Blood Pressure Monitoring".

(Continued)

*Primary Examiner* — Clayton E LaBalle
*Assistant Examiner* — Noam Reisner
(74) *Attorney, Agent, or Firm* — V. Gerald Grafe

(57) ABSTRACT

Example embodiments of the present invention provide methods and apparatuses that enable the detection of bubbles so that hemodynamic performance can be assured following an automated blood analyte measurement. An example apparatus according to the present invention comprises a blood access system, adapted to remove blood from a body and infuse at least a portion of the blood back into the body. The infusion of at least a portion of the blood back in to the body can be done in a manner to assure that no bubbles of clinical significance are injected into the patient. Additionally an example embodiment can assess for the presence of bubbles in the fluid column that can affect hemodynamic monitoring performance. If a condition exists where hemodynamic monitoring performance cannot be assured, an example embodiment can provide appropriate warning or corrective actions.

15 Claims, 21 Drawing Sheets

U.S. PATENT DOCUMENTS

| | | | |
|---|---|---|---|
| 5,697,366 A | 12/1997 | Kimball et al. | |
| 5,697,899 A | 12/1997 | Hillman et al. | |
| 5,709,534 A | 1/1998 | O'Leary | |
| 5,711,302 A * | 1/1998 | Lampropoulos et al. | 600/485 |
| 5,730,133 A | 3/1998 | Godik | |
| 5,758,643 A | 6/1998 | Wong et al. | |
| 5,830,132 A | 11/1998 | Robinson | |
| 6,006,119 A | 12/1999 | Soller et al. | |
| 6,017,318 A | 1/2000 | Gauthier et al. | |
| 6,027,445 A | 2/2000 | Von Bahr | |
| 6,128,519 A | 10/2000 | Say | |
| 6,201,980 B1 | 3/2001 | Darrow et al. | |
| 6,259,937 B1 | 7/2001 | Schulman et al. | |
| 6,304,767 B1 | 10/2001 | Soller et al. | |
| 6,356,675 B1 | 3/2002 | Weiss | |
| 6,366,726 B1 | 4/2002 | Wach et al. | |
| 6,391,643 B1 | 5/2002 | Chen et al. | |
| 6,477,395 B2 | 11/2002 | Schulman et al. | |
| 6,561,997 B1 | 5/2003 | Weitzel et al. | |
| 6,585,675 B1 | 7/2003 | O'Mahony et al. | |
| 6,618,603 B2 | 9/2003 | Varalli et al. | |
| 6,653,141 B2 | 11/2003 | Singaram et al. | |
| 6,707,135 B2 | 3/2004 | Madrid | |
| 6,809,826 B2 | 10/2004 | Robertson | |
| 6,817,984 B2 | 11/2004 | Robinson et al. | |
| 6,830,563 B1 | 12/2004 | Singer | |
| 6,876,931 B2 | 4/2005 | Lorenz et al. | |
| 6,887,214 B1 | 5/2005 | Levin et al. | |
| 6,916,424 B2 | 7/2005 | Collins et al. | |
| 6,918,874 B1 | 7/2005 | Hatch et al. | |
| 6,958,809 B2 | 10/2005 | Sterling et al. | |
| 6,989,891 B2 | 1/2006 | Braig et al. | |
| 6,990,366 B2 | 1/2006 | Say et al. | |
| 7,029,444 B2 | 4/2006 | Shin et al. | |
| 7,050,157 B2 | 5/2006 | Braig et al. | |
| 7,061,593 B2 | 6/2006 | Braig et al. | |
| 7,162,290 B1 | 1/2007 | Levin | |
| 7,398,183 B2 | 7/2008 | Holland et al. | |
| 2002/0121471 A1 | 9/2002 | Pedrazzi | |
| 2003/0086073 A1 | 5/2003 | Braig et al. | |
| 2003/0086074 A1 | 5/2003 | Braig et al. | |
| 2003/0086075 A1 | 5/2003 | Braig et al. | |
| 2003/0090649 A1 | 5/2003 | Sterling et al. | |
| 2004/0030277 A1 | 2/2004 | O'Mahony et al. | |
| 2004/0220517 A1 | 11/2004 | Starkweather et al. | |
| 2004/0241736 A1 | 12/2004 | Hendee | |
| 2004/0267100 A1 | 12/2004 | Faupel et al. | |
| 2005/0002018 A1 | 1/2005 | Erickson et al. | |
| 2005/0010093 A1 | 1/2005 | Ford et al. | |
| 2005/0027182 A1 | 2/2005 | Siddiqui et al. | |
| 2005/0038332 A1 | 2/2005 | Saidara et al. | |
| 2005/0049473 A1 | 3/2005 | Desai et al. | |
| 2005/0095602 A1 | 5/2005 | West et al. | |
| 2005/0143636 A1 | 6/2005 | Zhang et al. | |
| 2005/0230313 A1 | 10/2005 | O'Mahony et al. | |
| 2006/0009727 A1 | 1/2006 | O'Mahony et al. | |
| 2006/0052745 A1 | 3/2006 | Van Antwerp et al. | |
| 2006/0079809 A1 | 4/2006 | Goldberger et al. | |
| 2006/0127281 A1 * | 6/2006 | Bjornson et al. | 422/100 |
| 2006/0129109 A1 | 6/2006 | Shaw et al. | |
| 2006/0167381 A1 | 7/2006 | Azer et al. | |
| 2006/0173406 A1 | 8/2006 | Hayes et al. | |
| 2006/0183984 A1 | 8/2006 | Dobbles et al. | |
| 2006/0189857 A1 | 8/2006 | Faupel et al. | |
| 2006/0189858 A1* | 8/2006 | Sterling et al. | 600/310 |
| 2006/0189863 A1 | 8/2006 | Peyser et al. | |
| 2006/0189926 A1 | 8/2006 | Hall et al. | |
| 2006/0194325 A1 | 8/2006 | Gable et al. | |
| 2006/0195046 A1 | 8/2006 | Sterling et al. | |
| 2006/0195058 A1 | 8/2006 | Gable et al. | |
| 2006/0197015 A1 | 9/2006 | Sterling et al. | |
| 2006/0216209 A1 | 9/2006 | Braig et al. | |
| 2006/0229531 A1 | 10/2006 | Goldberger et al. | |
| 2006/0231424 A1 | 10/2006 | Harding et al. | |
| 2006/0235348 A1 | 10/2006 | Callicoat et al. | |
| 2006/0264895 A1 | 11/2006 | Flanders | |
| 2006/0268258 A1 | 11/2006 | Braig et al. | |
| 2006/0292650 A1 | 12/2006 | Braig et al. | |
| 2007/0038044 A1 | 2/2007 | Dobbles et al. | |
| 2007/0043334 A1 | 2/2007 | Guala | |
| 2007/0049809 A1 | 3/2007 | Bechtel et al. | |
| 2007/0060872 A1 | 3/2007 | Hall et al. | |
| 2007/0078314 A1 | 4/2007 | Grounsell et al. | |
| 2007/0082342 A1 | 4/2007 | Braig et al. | |
| 2007/0083091 A1 | 4/2007 | Sterling et al. | |
| 2007/0100222 A1 | 5/2007 | Mastrototaro et al. | |
| 2007/0104616 A1 | 5/2007 | Keenan et al. | |
| 2007/0177130 A1 | 8/2007 | MacIntyre et al. | |
| 2007/0179436 A1 | 8/2007 | Braig et al. | |
| 2007/0213657 A1 | 9/2007 | Jennewine et al. | |
| 2007/0225675 A1 | 9/2007 | Robinson et al. | |
| 2007/0240497 A1 | 10/2007 | Robinson et al. | |
| 2007/0244381 A1 | 10/2007 | Robinson et al. | |
| 2007/0244382 A1 | 10/2007 | Robinson et al. | |
| 2008/0014601 A1 | 1/2008 | Goldberger et al. | |
| 2009/0043240 A1 | 2/2009 | Robinson et al. | |
| 2009/0054753 A1 | 2/2009 | Robinson et al. | |
| 2009/0054754 A1 | 2/2009 | McMahon et al. | |
| 2009/0149795 A1 | 6/2009 | O'Mahony | |
| 2009/0156975 A1 | 6/2009 | Robinson et al. | |

FOREIGN PATENT DOCUMENTS

| | | |
|---|---|---|
| WO | PCT/US05/034740 | 4/2006 |
| WO | PCT/EP06/010765 | 5/2007 |

OTHER PUBLICATIONS

Cardinal Health, "Reducing Variability in High Risk Intravenous Medication Use", Center for Medication Safety and Clinical Improvement, 2005.

Chee et al, IEEE transactions on information technology in biomass and, vol. 7, No. one, Mar. 2003.

Davidson et al., "Glucommander", Diabetes Care, vol. 28, No. 10, Oct. 2005.

DRA Staff, "Report of the Automated Control of Insulin Levels Committee", Committee Report (DRA 5), Institute for Alternative Futures, p. 9, Sep. 2006.

Enejder et al., 2003, Applied Optics, v42, p1384, Influence of cell shape and aggregate formation on the optical properties of flowing whole blood.

Fessler, H.E., "Heart—lung interactions: applications in the critically ill", European Respiratory Journal, 1997; 10: 226-237.

Ford, Anne; Bedside Glucose Testing Systems, CAP today, Apr. 2006, p. 44.

Gardner 1981, "Direct Blood Pressure Measurements—Dynamic Response Requirements" Anesthesiology v54, pp. 227-236.

Goldberg et al. "Experience with continuous glucose monitoring system in a medical intensive care unit" Diabetes Technology and Therapeutics, vol. 6, No. 3, 2004.

Gough et al. In Two-Dimensional Enzyme Electrode Sensor for Glucose, vol. 57, Analytical Chemistry pp. 2351 et seq (1985).

Hickam et al (J. Biol. Chem., 1949, vol. 180, No. 1, p. 457-465).

Holt JP, The effect of positive and negative intrathoracic pressure on cardiac output and venous return in the dog. Am J Physiol 1944; 142:594-603.

Hovorka, "Continuous glucose monitoring and closed-loop systems," Diabetes Med v23, p. 1-12, 2005.

http://www.2aida.net/welcome/, visited Jun. 10, 2010.

Krinsley et al., Mayo Clin Proc, 78, 1471 (2003).

MacKenzie, Iain et al., "Tight glycemic control:a survey of intensive care practice in large English Hospitals;" Intensive Care Med (2005) 31 :1136.

Morgan BC, Martin WE, Hornbein TF, et al. Hemodynamic effects of intermittent positive pressure respiration. Anesthesiology 1966, 27:584-590.

Oye et al.; "Patterns of resource consumption in medical intensive care," (Chest 99:685,1991).

Pinsky, Michael, "Cardiovascular Issues in Respiratory Care", Chest 2005: 128: 592-597.

Taylor et al., Journal of American College of Surgeons, 202, 1 (2006).

Tobin, Principles and Practice of Mechanical Ventilation, 2nd Edition, Chapt 36, McGraw-Hill, copyright 2006.

Utzinger and Richards-Kortum "Fiber optic probes for biomedical optical spectroscopy", J. Biomedical Optics 8(1), 121 (2003).

Van Den Berghe et al., "Intensive Insulin Therapy in Critically Ill Patients", NEJM 2001; 345:1359, Nov. 8, 2001.

Vriesendorp et al., "The use of two continuous glucose sensors during and after surgery," Diabetes Technology and Therapeutics, vol. 7, No. 2, 2005.

Workman, ASTM International E 1655-05, "Standard Practices for Infrared Multivariate Quantitative Analysis," Copyright © ASTM International, 100 Barr Harbor Drive, PO Box C700, West Conshohocken, PA 19428-2959, United States, 2007.

Bergman, Assessment of Insulin Sensitivity in Vivo, Endocrine Reviews 6(1):45, 1985.

Chevalier PA, Weber KC, Engle JC, et al. Direct measurement of right and left heart outputs in ValSalva-like maneuver in dogs. Proc Soc Exper Biol Med 1972; 139:1429-1437.

Garland et al., Physician-attributable Differences in Intensive Care Unit Costs, American Journal of Respiratory and Critical Care Medicine vol. 174, 2006.

Gunteroth WC, Gould R, Butler J, et al. Pulsatile flow in pulmonary artery, capillary and vein in the dog. Cardiovascular Res 1974; 8:330-337.

Guntheroth WG, Morgan BC, Mullins GL, Effect of respiration on venous return and stroke volume in cardiac tamponade. Mechanism of pulsus paradoxus. Circ Res 1967; 20:381-390.

Heise et al., Ex vivo determination of blood glucose by microdialysis in combination with infrared attenuated total reflection spectroscopy, Fresenius J Anal Chem, 1997, vol. 359, p. 83-87.

J. Lin, Geoff Chase, Geoff Shaw, et al. at the University of Canterbury—"Long-term Verification of Glucose—Insulin Regulatory System Model Dynamics" at the 26th Annual International Conference of the IEEE Engineering in Medicine and Biology Society, 2004.

Morgan BC, Abel FL, Mullins GL, et al. Flow patterns in cavae, pulmonary artery, pulmonary vein and aorta in intact dogs. Am J Physiol 1966; 210; 903-909.

Morgan, B.C., et al., Hemodynamic Effects of Intermittent Positive Pressure Respiration, Anesthesiology 1966.

Tanaka et al. (Applied Optics, 1975, vol. 14, No. 1, p. 189-196), Measurement of the velocity of blood flow in vivo using a fiber optic catheter and optical mixing spectroscopy.

Thevenot, Problems in Adapting a Glucose-Oxidase Electrochemical Sensor into an Implantable Glucose-Sensing Device, (Diabetes Care, vol. 5 No. 3:184-189) 1982.

* cited by examiner

DETECTION OF BUBBLES DURING HEMODYNAMIC MONITORING WHEN PERFORMING AUTOMATED MEASUREMENT OF BLOOD CONSTITUENTS

CROSS REFERENCE TO RELATED APPLICATIONS

This application is related to the following patent applications, each of which is incorporated herein by reference: U.S. provisional 60/791,719, filed Apr. 12, 2006; U.S. provisional 60/913,582, filed Apr. 24, 2007; PCT application PCT/US06/60850, filed Nov. 13, 2006; U.S. application Ser. No. 11/679,826, filed Feb. 27, 2007; U.S. application Ser. No. 11/679,837, filed Feb. 28, 2007; U.S. application Ser. No. 11/679,839, filed Feb. 28, 2007; U.S. application Ser. No. 11/679,835, filed Feb. 27, 2007; U.S. application Ser. No. 10/850,646, filed May 21, 2004; U.S. application Ser. No. 11/842,624, filed Aug. 21, 2007; U.S. application Ser. No. 12/188,205, filed Aug. 8, 2008; U.S. provisional 60/991,373, filed Nov. 30, 2007; U.S. provisional 61/044,004, filed Apr. 10, 2008; U.S. application Ser. No. 12/108,250 filed Apr. 23, 2008; U.S. provisional 61/204,193 filed Oct. 9, 2008; U.S. application Ser. No. 12/576,121, filed Oct. 8, 2009.

BACKGROUND

Since 2001, a number of intensive care units have adopted glycemic control protocols for the maintenance of glucose at close to physiological levels. The process of maintaining tight glycemic control requires frequent blood glucose measurements. The blood utilized for these measurements is typically obtained by procurement of a sample from a fingerstick, arterial line, or central venous catheter. Fingerstick measurements are generally considered undesirable due to the pain associated with the fingerstick process and the nuisance associated with procurement of a quality sample. Sample procurement from central venous catheters can also present problems since current clinical protocols recommend the stoppage of all fluid infusions prior to the procurement of a sample. Consequently, the use of arterial catheters has become more common. Arterial blood gas catheters are typically placed for hemodynamic monitoring of the patient, also referred to as real-time continuous blood pressure monitoring. These catheters are maintained for a period of time and used for both hemodynamic monitoring and blood sample procurement. Arterial blood gas catheters are not used for drug or intravenous feedings so issues associated with cross-contamination are minimized.

The process of procuring an arterial blood sample for measurement typically involves the following steps. The slow saline infusion used to keep the artery open is stopped and some type of valve mechanism such as a stopcock is opened to allow fluid connectivity to the mechanism for blood draw. The process of opening the stopcock and concurrently closing off fluid connectivity to the pressure transducer will cause a stoppage of patient pressure monitoring as the transducer no longer has direct fluid access to the patient. The sample procurement process is initiated. The initial volume drawn through the stopcock is saline followed by a transition period of blood and saline and subsequently pure blood. Generally, at the point where there is no or very little saline in the blood sample at the stopcock (or a knowable saline concentration), the measurement sample is obtained. The blood and saline sample obtained previously can be discarded or infused back into the patient.

In many intensive care units, a significant portion of blood samples obtained from arterial catheters are procured using blood sparing systems. In this process a leading sample containing both saline and blood is withdrawn from the patient and stored in a reservoir that lies beyond the sample acquisition port. A sample of blood that is free of saline contamination can then be procured at the sample port for measurement. Example embodiments of such blood sparing techniques include the Edward's VAMP system, shown in FIG. 1, and the Abbott SafeSet system. The Edward's VAMP in-service poster is incorporated by reference. Following procurement of an undiluted sample for measurement, the remaining blood/saline mixture can be re-infused into the patient. FIG. 1 is a schematic depiction of Edward's VAMP Plus System, an example blood sparing device. In the example device, a blood access system attached to arterial line, blood withdrawn and re-infused. A pressure monitoring transducer is remote from patient (60 inches). The tubing used between patient and pressure transducer is very stiff so compliance is minimized. A saline wash of transducer is provided after a clean sample is drawn into the syringe.

Air bubbles represent a significant problem for hemodynamic monitoring systems as they change the overall performance of the system. Air bubbles can become trapped in the monitoring system during filling, blood sampling, or added later by manual flushing or continuous flush devices. The presence of an air bubble adds undesirable compliance to the system and tends to decrease the resonant frequency and increase the damping coefficient. The resonant frequency typically falls faster than the damping increases, resulting in a very undesirable condition. FIG. 2 illustrates the effect of adding microliter air bubbles of various sizes to a transducer-tubing system. As more and more air is added to the system, the decrease in resonant frequency produces larger and larger errors in the systolic pressure, even though damping is increasing at the same time. Eventually, so much air could be added that the system produces only damped sine waves. Air bubbles diminish, not enhance, the performance of blood pressure monitoring systems. The preceding information was obtained from the Association for the Advancement of Medical Instrumentation, technical information report titled "Evaluation of clinical systems for invasive blood pressure monitoring".

In clinical use, a pressure monitoring system should be able to detect changes quickly. This is known as its "frequency response". The addition of damping to a monitoring system will tend to decrease its responsiveness to changes in the frequency of the pressure waveform but prevents unwanted resonances. This is especially so if changes are occurring rapidly such as occur at high heart rates or with a hyperdynamic heart. During these conditions it is essential that the system have a high "natural" or "untamed" frequency response. The optimal pressure monitoring system should have a high frequency such that over damped or under damped waveforms are unlikely regardless of the degree of damping present. The relationship of frequency and camping coefficient have been explored and defined by Reed Gardner. This relationship is well described in "Direct Blood Pressure Measurements—Dynamic Response Requirements" anesthesiology pages 227-23 6, 1981, incorporated herein by reference. FIG. 3 shows the resulting relationship between damping and natural frequency.

Due to the existing performance requirements and the fact that air bubbles dramatically alter the performance of a typical hemodynamic monitoring system, it is clinical practice to have the clinician evaluate the system carefully for the presence of any air bubbles. As stated by Michael Cheatham in "Hemodynamic Monitoring: Dynamic Response Artifacts" (available from www.surgicalcriticalcare.net), perhaps the single most important step in optimizing dynamic response is ensuring that all transducers, tubing, stopcock, and injection ports are free of air bubbles. Air, by virtue of being more compressible than fluid, tends to act as a shock absorber within a pressure monitoring system leading to a over damped waveform with its attendant underestimation of systolic blood pressure and over estimation of diastolic blood pressure. The identification of air bubbles is typically done by visual inspection of the system as well as by a dynamic response test. In practice this dynamic response test is achieved by doing a fast—flush test. A fast flesh or square wave test is performed by opening the valve of the continuous flush device such that flow through the catheter tubing is actually increased to approximately 30 ml/hr versus the typical 1-3 ml/hr. This generates an acute rise in pressure within the system such that a square wave is generated on the bedside monitor. With closure of the valve, a sinusoidal pressure wave of a given frequency and progressively decreasing implicated is generated. A system with appropriate dynamic response characteristics will return to the baseline pressure waveform within one or two oscillations, as illustrated in FIG. 4. If the fast—flush technique produces dynamic response characteristics that are inadequate, the clinician should troubleshoot the system to remove air bubbles, minimize tubing junctions, etc., until acceptable dynamic response is achieved.

In almost any automated blood glucose monitoring system, the device must procure or withdraw a sample of blood from the body. This process may require a few milliliters of blood or only a few micro liters. Regardless of the amount, the process exposes the associated fluid column to pressure gradients, potentially different pressures and fluid flows. Therefore, the process of procuring a blood sample has the potential to create bubbles within the fluid column. The fluid column is not intended to be restrictive but to apply to any of the fluid associated with the automated sample measurement system. Solubility is the property of a solid, liquid or gas called solute to dissolve in a liquid solvent to form a homogeneous solution. The solubility of a substance strongly depends on the used solvent as well as on temperature and pressure. In the application of automated blood measurements, the liquid solvent is blood, saline or any intravenous solution. The solute is air, oxygen or any gas in the liquid solvent. Changers in solubility due to temperature or pressure may result in bubble formation. As a solution warms it will typically outgas due to a decrease in solubility with temperature. Changes in pressure can also result in bubbles. The solubility of gas in a liquid increases with increasing pressure. Henry's Law states that: the solubility of a gas in a liquid is directly proportional to the pressure of that gas above the surface of the solution. If the pressure is increased, the gas molecules are forced into the solution since this will best relieve the pressure that has been applied.

Bubbles may be formed due to cavitation. Cavitation is the formation of bubbles in a flowing liquid in a region where the pressure of the liquid falls below its vapor pressure. Cavitation can occur due to pumping at the low pressure or suction side of the pump. Cavitation can occur via multiple methods but the most common are vaporization, air ingestion (not always considered cavitation, but has similar symptoms), and flow turbulence In a typical process of procuring a blood sample, a negative or reduced pressure is created so that the blood flows out of the body. This reduction in pressure creates an opportunity for bubble creation. Additionally, temperature differences between the human body, the ambient air, and any IV solutions also create the opportunity for bubble creation. Almost any form of pumping device creates some small degree of cavitation. Therefore, the process of attaching or combining a hemodynamic monitoring system with an automated blood measurement system creates the opportunity for bubble formation which in turn can result in poor performance of the hemodynamic monitoring system.

SUMMARY OF THE INVENTION

Example embodiments of the present invention provide methods and apparatuses that enable the detection of bubbles so that hemodynamic performance can be assured following an automated blood analyte measurement. An example apparatus according to the present invention comprises a blood access system, adapted to remove blood from a body and infuse at least a portion of the blood back into the body. The infusion of at least a portion of the blood back in to the body can be done in a manner to assure that no bubbles of clinical significance are injected into the patient. Additionally an example embodiment can assess for the presence of bubbles in the fluid column that can affect hemodynamic monitoring performance. If a condition exists where hemodynamic monitoring performance cannot be assured, an example embodiment can provide appropriate warning or corrective actions.

An example method according to the present invention can comprise a bubble detection system used in conjunction with an automated analyte measurement and a hemodynamic monitoring system. The description herein will refer to an example blood access system for convenience. Other blood access systems and other analyte measurement techniques are also suitable for use with the present invention, as examples including those described in the patent applications incorporated by reference herein.

Some example embodiments of the present invention provide for the detection of bubbles that would adversely impact the performance of the hemodynamic monitoring system. Some example embodiments of the present invention provides for both the detection of bubbles that can adversely impact the performance of the hemodynamic monitoring system and provide for a mechanism to remove these bubbles. Some example embodiments of the present invention can minimize the formation of bubbles during the automated blood measurement process.

BRIEF DESCRIPTION OF THE DRAWINGS

The accompanying figures are incorporated into and form part of the specification, and, with the specification, illustrate example embodiments of the present invention.

EXAMPLE EMBODIMENTS OF THE PRESENT INVENTION

Example embodiments of the present invention provide methods and apparatuses that enable the detection of bubbles so that hemodynamic performance can be assured following an automated blood analyte measurement. An example apparatus according to the present invention comprises a blood access system, adapted to remove blood from a body and infuse at least a portion of the blood back into the body. The infusion of at least a portion of the blood back in to the body can be done in a manner to assure that no bubbles of clinical significance are injected into the patient. Additionally an example embodiment can assess for the presence of bubbles in the fluid column that can affect hemodynamic monitoring performance. If a condition exists where hemodynamic monitoring performance cannot be assured, an example embodiment can provide appropriate warning or corrective actions.

An example method according to the present invention can comprise a bubble detection system used in conjunction with an automated analyte measurement and a hemodynamic monitoring system. The description herein will refer to an example blood access system for convenience. Other blood access systems and other analyte measurement techniques are also suitable for use with the present invention, as examples including those described in the patents and patent applications incorporated by reference herein.

Some example embodiments of the present invention provide for the detection of bubbles that would adversely impact the performance of the hemodynamic monitoring system. Some example embodiments of the present invention provide for both the detection of bubbles that can adversely impact the performance of the hemodynamic monitoring system and provide for a mechanism to remove these bubbles. Some example embodiments of the present invention can minimize the formation of bubbles during the automated blood measurement process.

Figure 5:
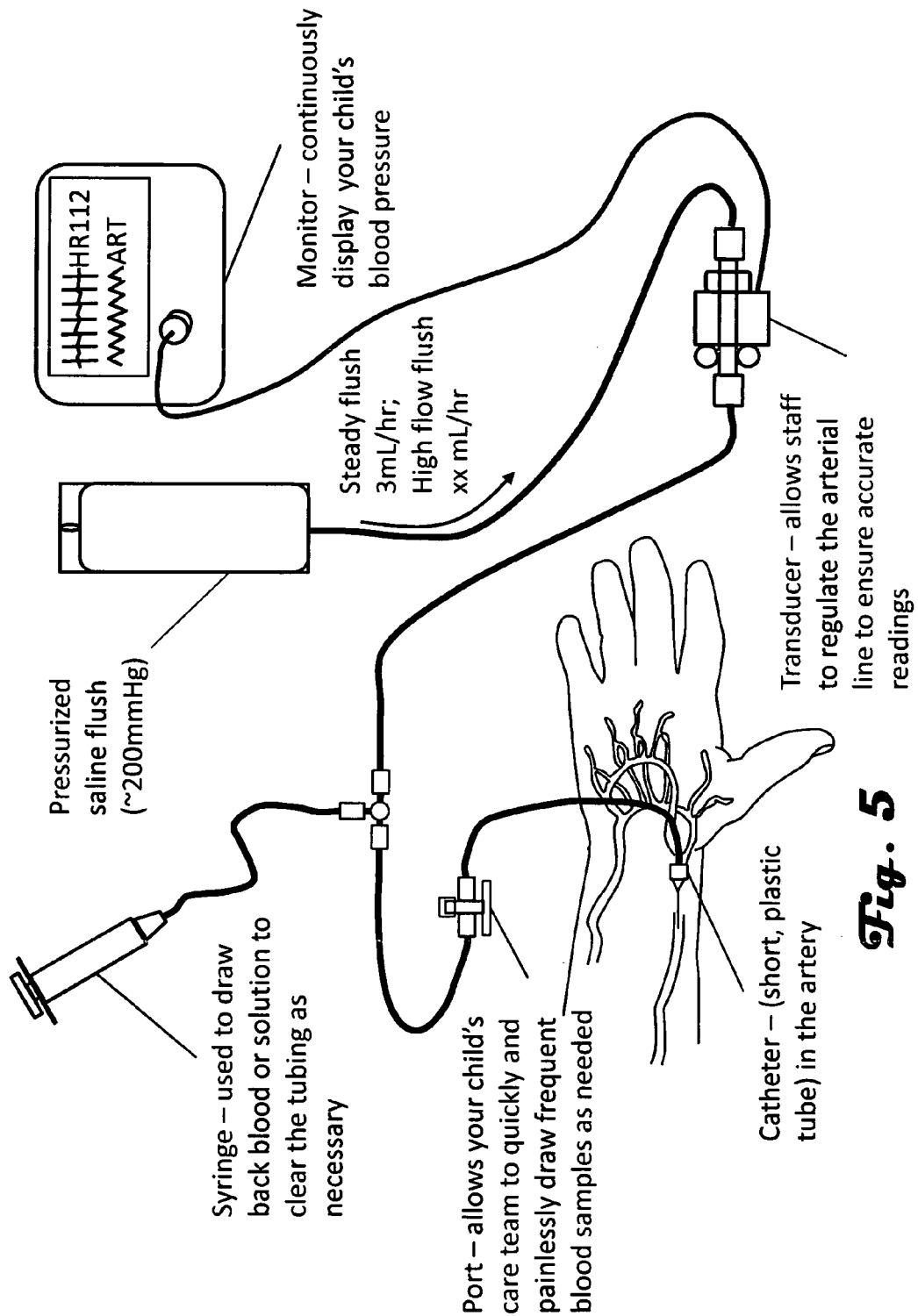
FIG. 5 is a schematic depiction of an arterial catheter pressure monitoring configuration.

An ICU (intensive care unit) pressure monitoring application is illustrated in FIG. 5. A pressure transducer is in direct contact with the arterial blood via a fluid column or stream. In typical operation a pressurized saline bag is used to infuse a small amount of saline into the patient at a constant rate. This saline infusion helps to keep the access site open. During a typical blood withdrawal sequence, the stopcock at the pressure transducer is closed and a sample is procured by a syringe attached to the arterial catheter. During this period of time no hemodynamic monitoring occurs. Following completion of the blood sample procurement, the stopcock is again opened and hemodynamic monitoring is reinitiated. The nurse or clinician will typically examine the arterial waveform for artifacts and inspect the tubing to ensure that no bubbles are present.

Figure 1:
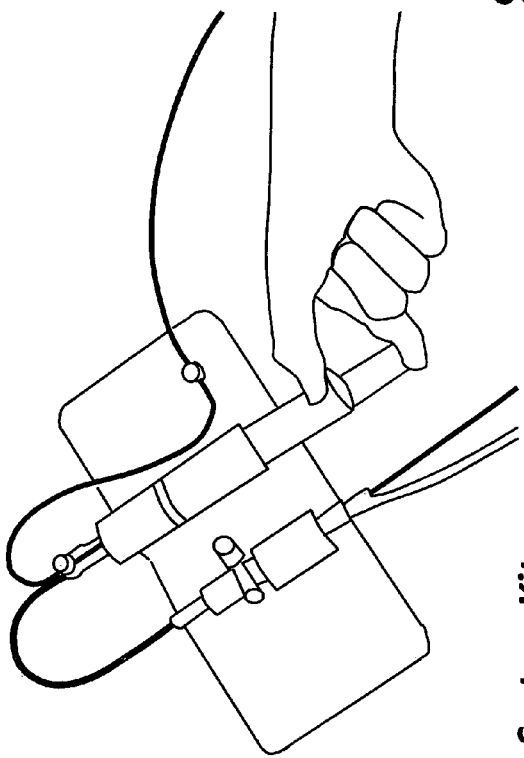
FIG. 1 is a schematic depiction of Edward's VAMP Plus System, an example blood sparing device.
Figure 2:
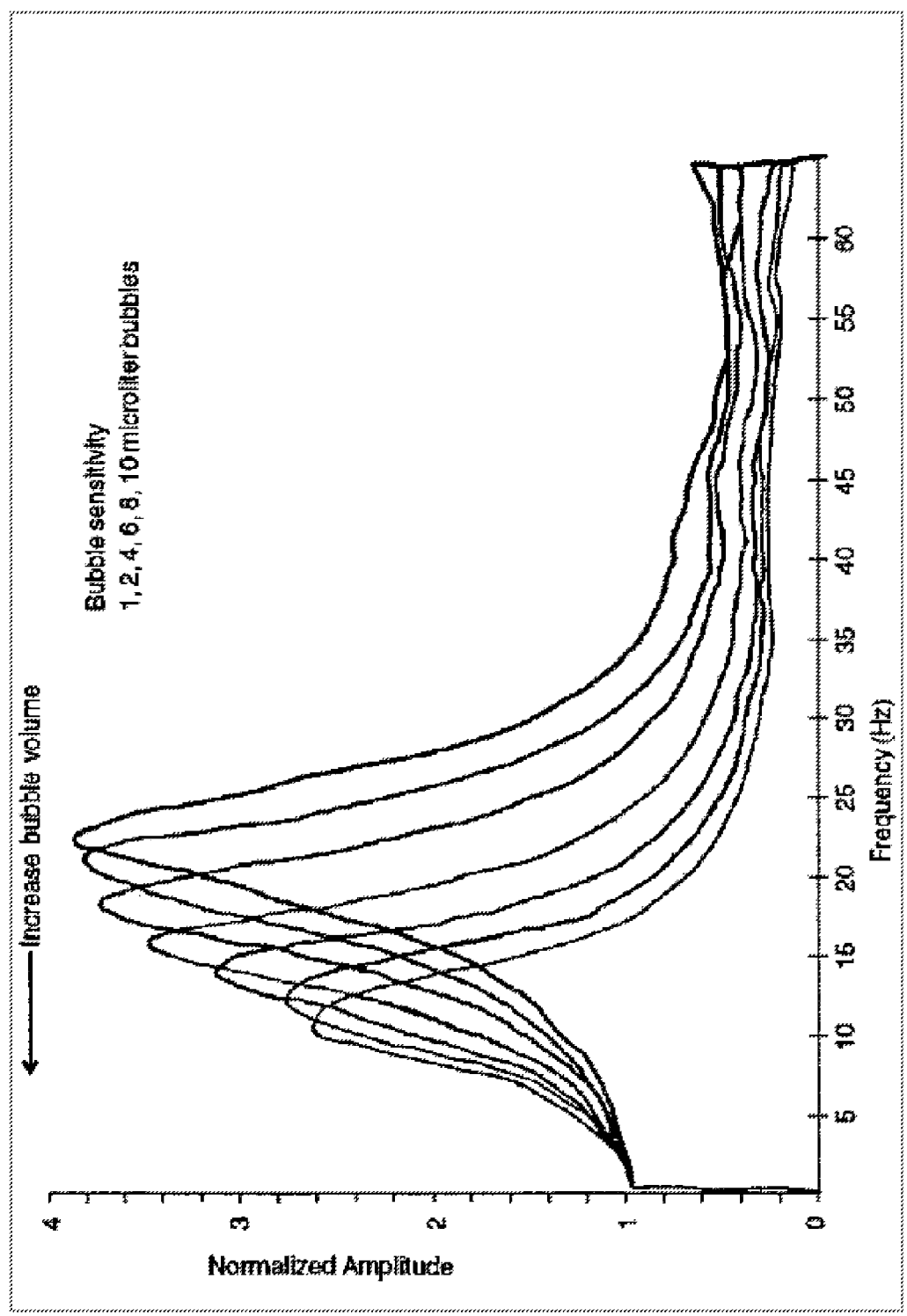
FIG. 2 is an illustration of the effect of adding microliter air bubbles of various sizes to a transducer tubing system.
Figure 3:
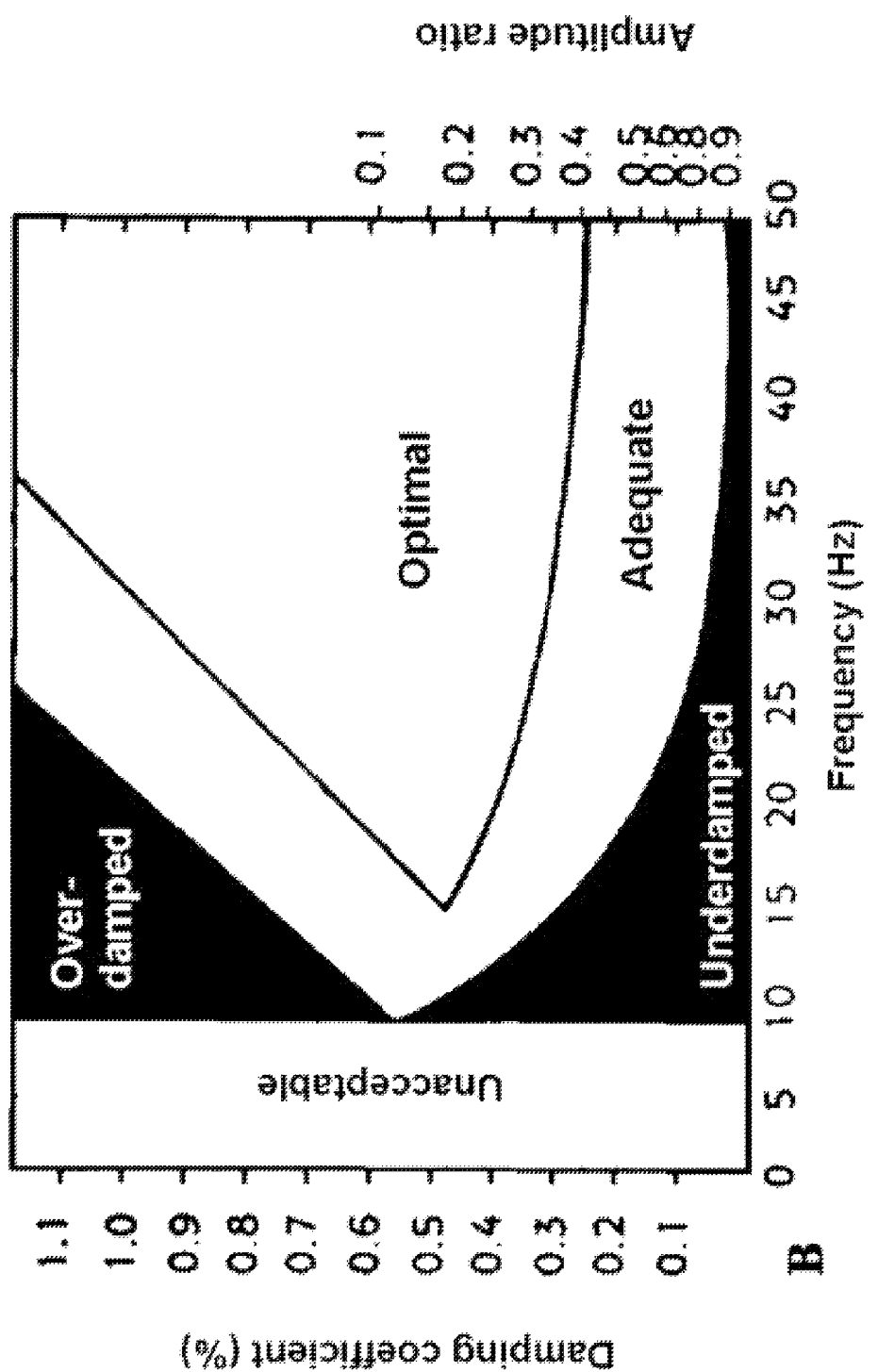
FIG. 3 is an illustration of Gardner's wedge showing the relationship between damping and frequency.
Figure 4:
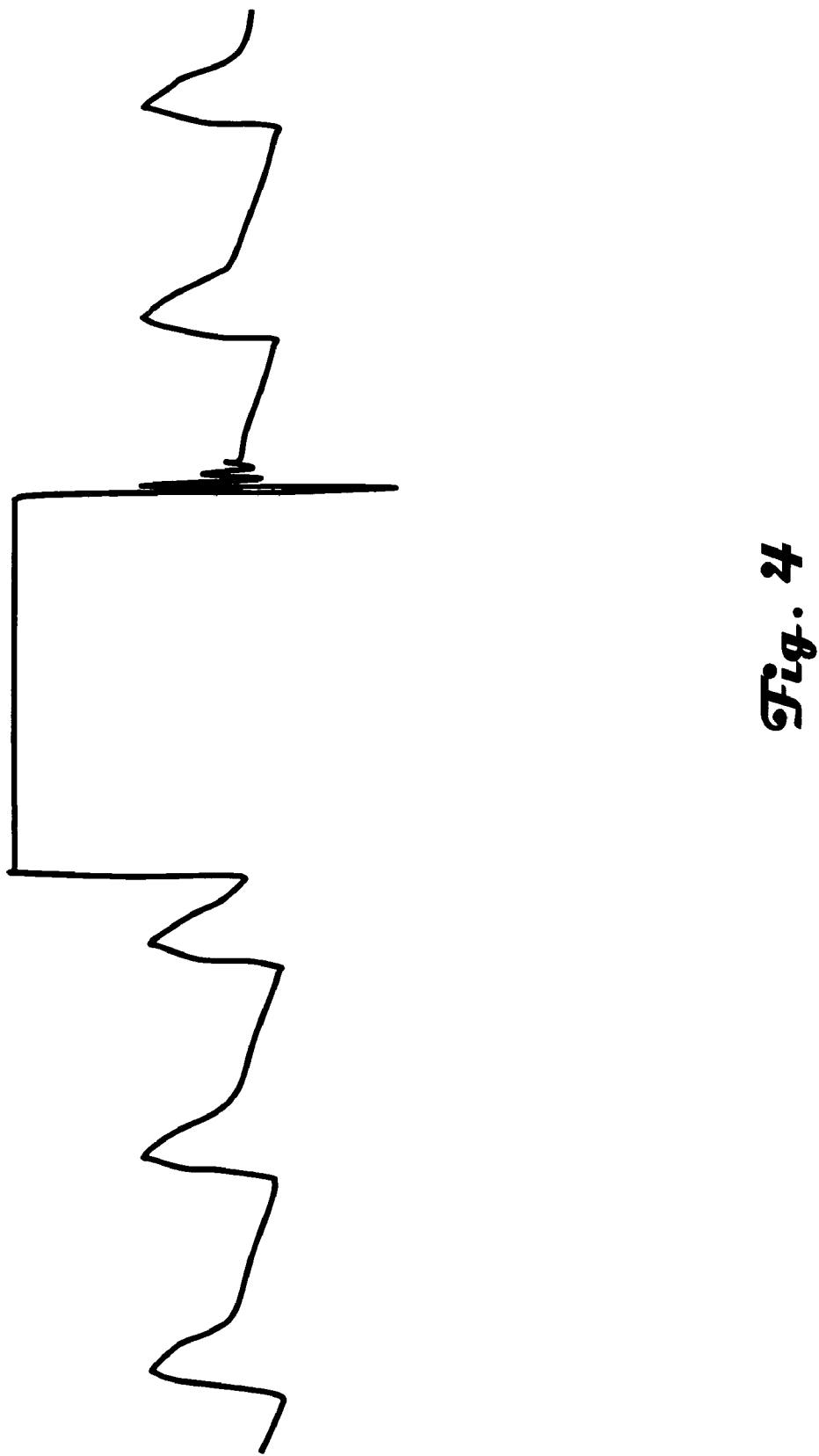
FIG. 4 is an illustration of an example arterial waveform tracing obtained from a monitoring system following a fast flush technique.
Figure 6:
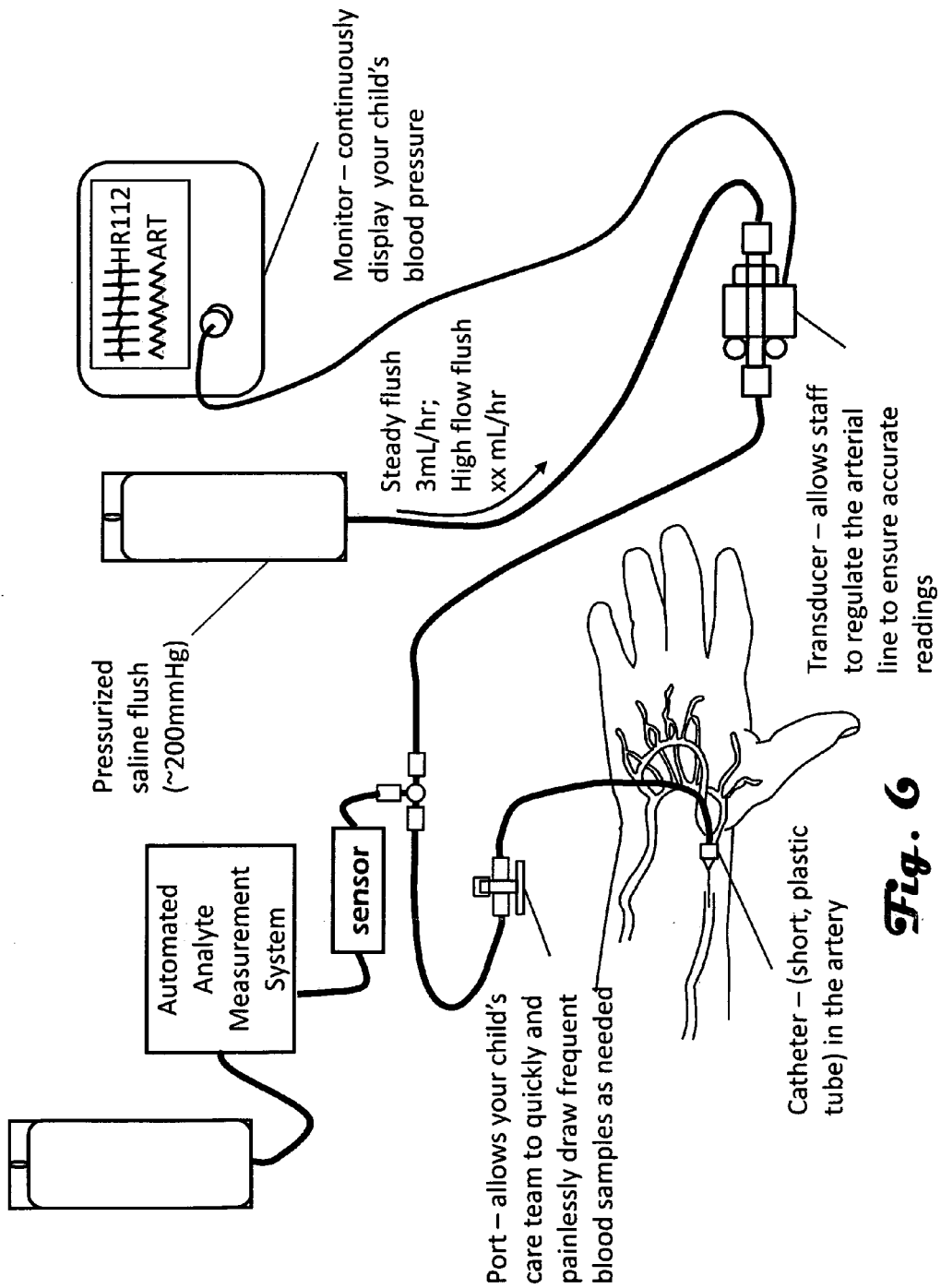
FIG. 6 is a schematic depiction of an arterial catheter pressure monitoring configuration with an automated analyte measurement system.

As shown in FIG. 6 an automated sample acquisition and analyte measurement system (e.g., a measurement system that measures one or more analytes in blood, such as glucose, arterial blood gasses, lactate, hemoglobin, and urea) can be attached to a similar system in a manner similar to the syringe blood withdrawal port illustrated in FIG. 5. If the process is to be automated, the patient, the pressure transducer and the analyte measurement system are in fluid connection. By fluid connection, it denotes a condition where fluid can travel between the patient, the analyte measurement system and the pressure transducer without changes to the system or the opening or closing of valves. If during sample procurement by the automated analyte measurement system an air bubble is created it can have some degree of adverse impact on the hemodynamic monitoring system due to the bubble being in fluid connection with the pressure transducer. The impact of the bubble can vary depending upon both size and location in the system. As shown in FIG. 2 even a small bubble can result in inaccurate pressure measurements.

Figure 7:
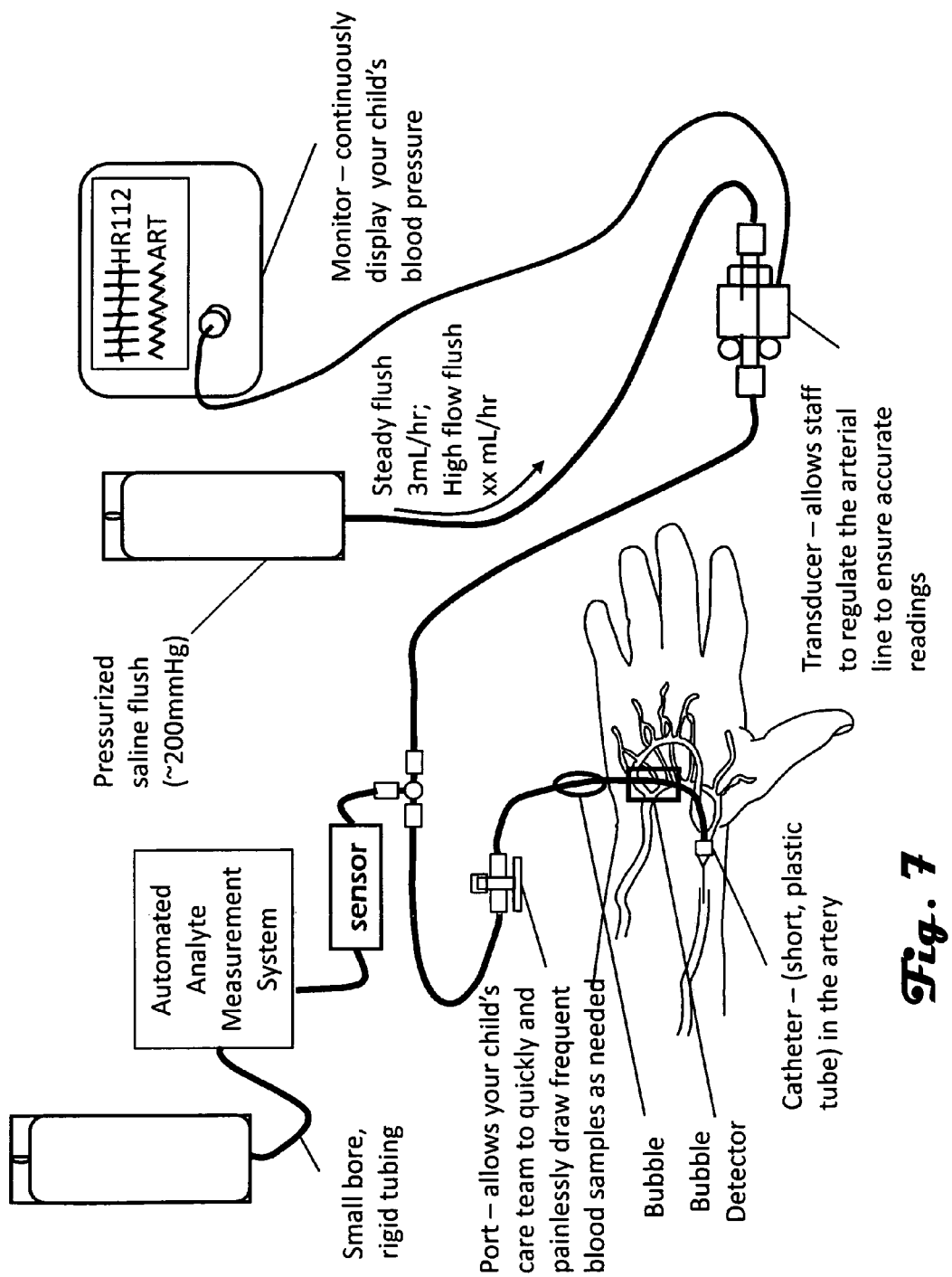
FIG. 7 is a schematic depiction of a bubble and a fluid column.

FIG. 7 illustrates a potentially problematic condition where a bubble is present between patient and the pressure transducer but removed from the bubble detector. The detection of such a bubble in this section of tubing is problematic and would historically have required visual inspection of the system or a fast-flush hemodynamic test administered by the clinician.

The present invention can address such a situation by comparing characteristics of the arterial waveform from before a sample procurement (or "draw") with characteristics following of the arterial waveform following sample procurement. For illustrative purposes consider the process where the clinician establishes both the hemodynamic monitoring system as well as the automated analyte measurement system and assures that appropriate performance is present in the hemodynamic monitoring system. At this point in time, it can be assumed that there are no significant bubbles in the system that adversely influence hemodynamic monitoring performance. Consider this condition as baseline performance. The arterial waveform at baseline or prior to an automated draw can be determined and stored for future examination. The automated measurement system procures a sample for measurement. As noted above, the procurement and measurement process has the potential to introduce bubbles into the system. If the bubbles pass the bubble detector then the bubble can easily be detected. In an alternative situation, operation of the system can create a bubble, but the bubble does not interact with the bubble detector. Following completion of the automated analyte measurement, it is desirable to reinitiate hemodynamic monitoring. However, a bubble present in the fluid system it can adversely impact the accuracy of future pressure measurements. Prior to displaying hemodynamic measurements, the system can compare the pre-measurement arterial waveform with a post-measurement arterial waveform for the detection of a bubble or bubbles.

Figure 8:
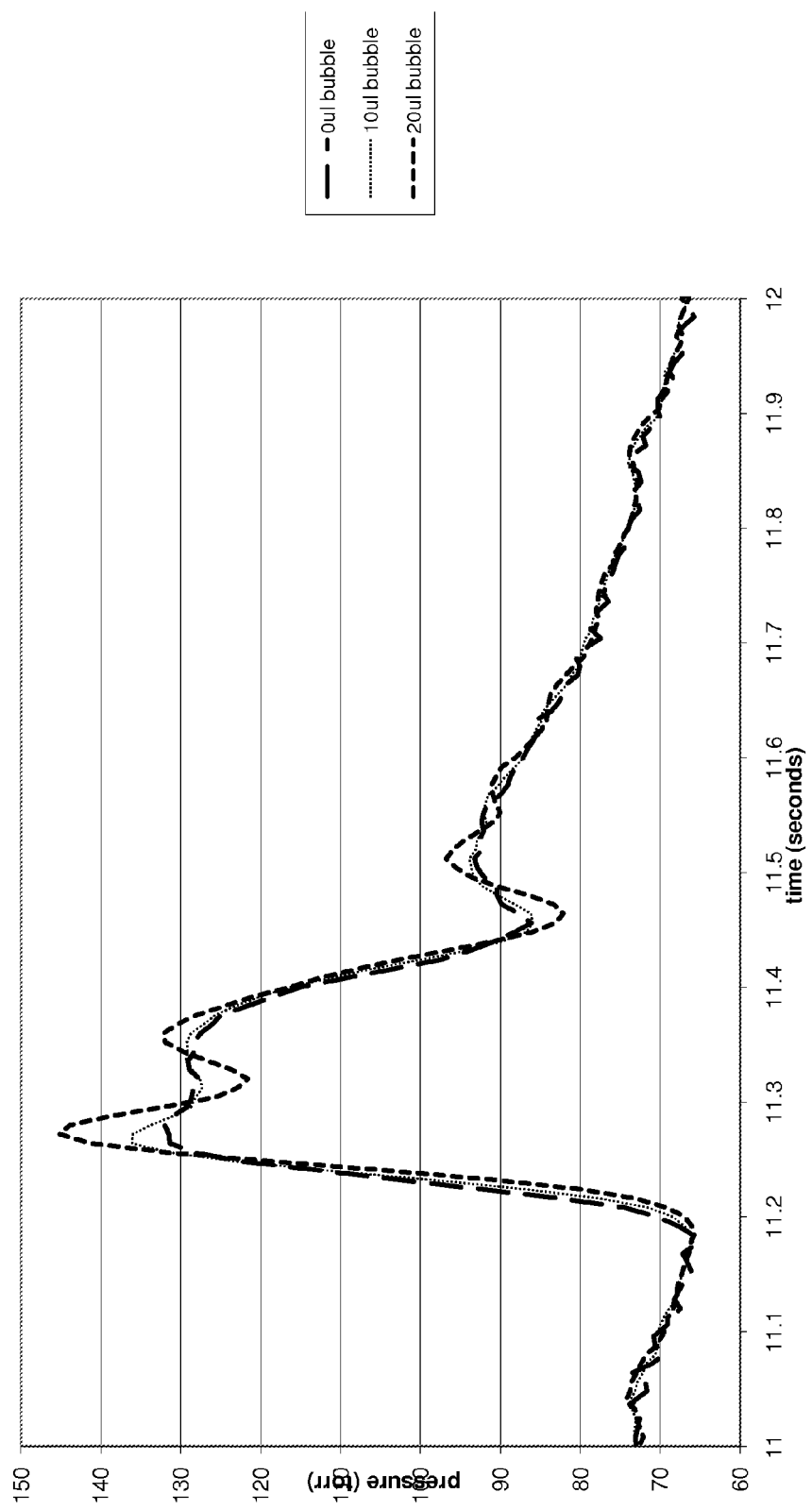
FIG. 8 is a schematic depiction of the influence of bubbles on a measured arterial waveform.

FIG. 8 illustrates the results of a laboratory test that illustrates the impact of bubbles on the resulting recorded waveform. In the laboratory tests, a variable pressure device was programmed to reproduce an arterial waveform. A standard blood pressure transducer in a standard clinical configuration was attached to the variable pressure device and waveform recordings were initiated. An initial test with no air bubbles in the line was recorded. Also recorded was a waveform tracing with a 10 µL bubble present, and a waveform tracing with a 20 µL bubble present. Examination of the corresponding waveforms illustrates that the presence of bubbles in the fluid path causes distortions in the true signal. Examination of the plot shows approximately a 5 mm Hg measurement error for the 10 µL bubble in the systolic pressure readings. The error is approximately 15 mm Hg for the 20 µL bubble. Additionally, the system exhibits signs of being under damped and thus shows some ringing after rapid changes.

A comparison between the pre-measurement waveform and post measurement waveforms can enable the detection of a bubble or bubbles that can affect hemodynamic performance. This comparison can take many forms to include simple subtraction, division, Fourier transform analysis, wavelet analysis, vector comparison, derivative processing, or any other mathematical treatment that enables a comparison between the two waveforms whereby the presence of a bubble can be detected. Other less common methods could be Functional Data Analysis, various pattern recognition methods to include not limited to compound term processing, computer-aided diagnosis, machine learning, neocognitron, predictive analytics and template matching. Other potential methods could include Hierarchical Temporal Memory. HTM, and is applicable to a broad class of problems from machine vision, to fraud detection, to semantic analysis of text. HTM is based on a theory of neocortex first described in the book On Intelligence by Jeff Hawkins.

Figure 9:
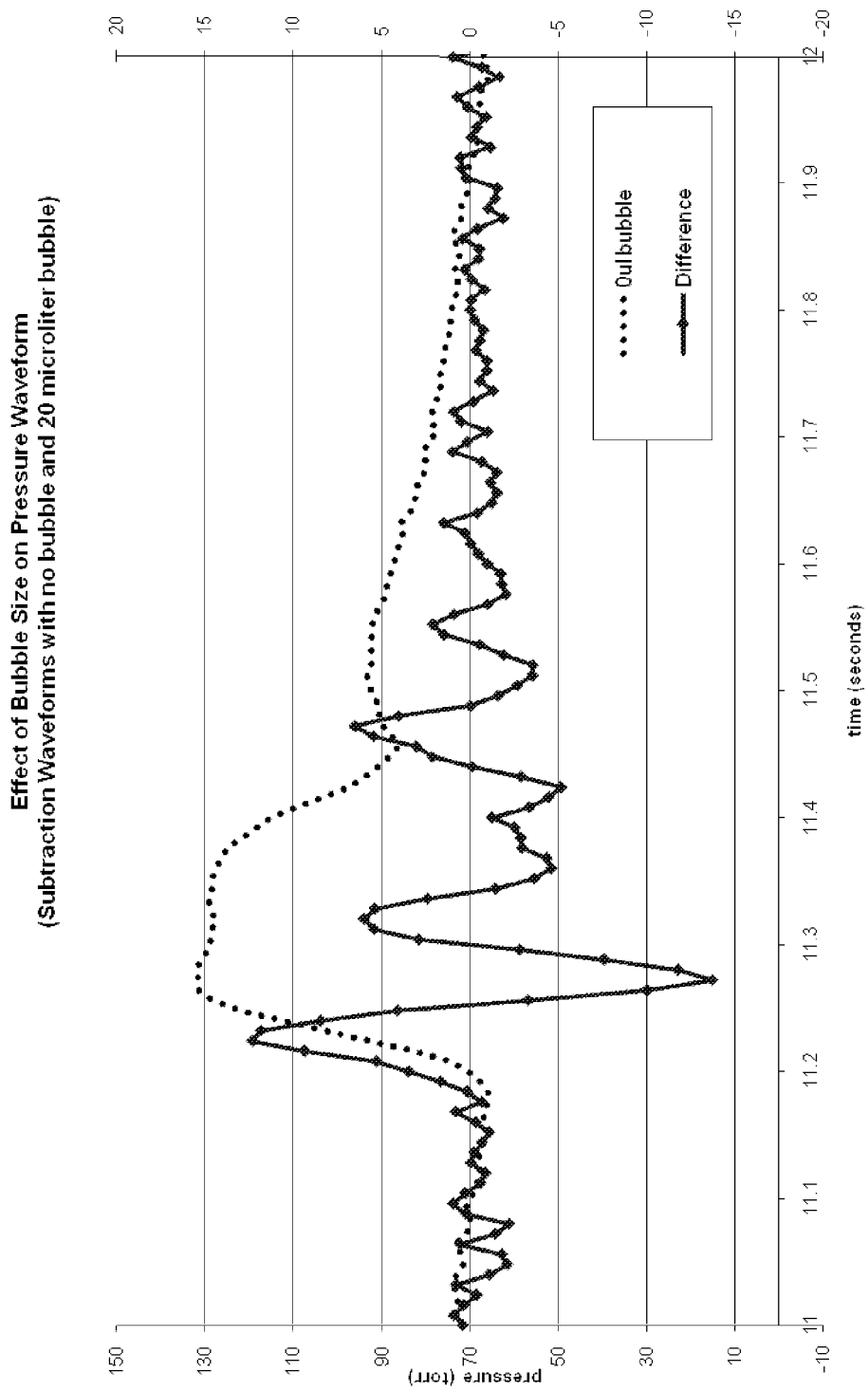
FIG. 9 is a schematic depiction of the difference between measured waveforms.

For illustrative purposes FIG. 9 shows a simple subtraction between a waveform with no bubble and a waveform with a 20 µL bubble. The resulting differences are large at the systolic peak and a simple threshold comparison can be used to detect the potential presence of a bubble.

Figure 10:
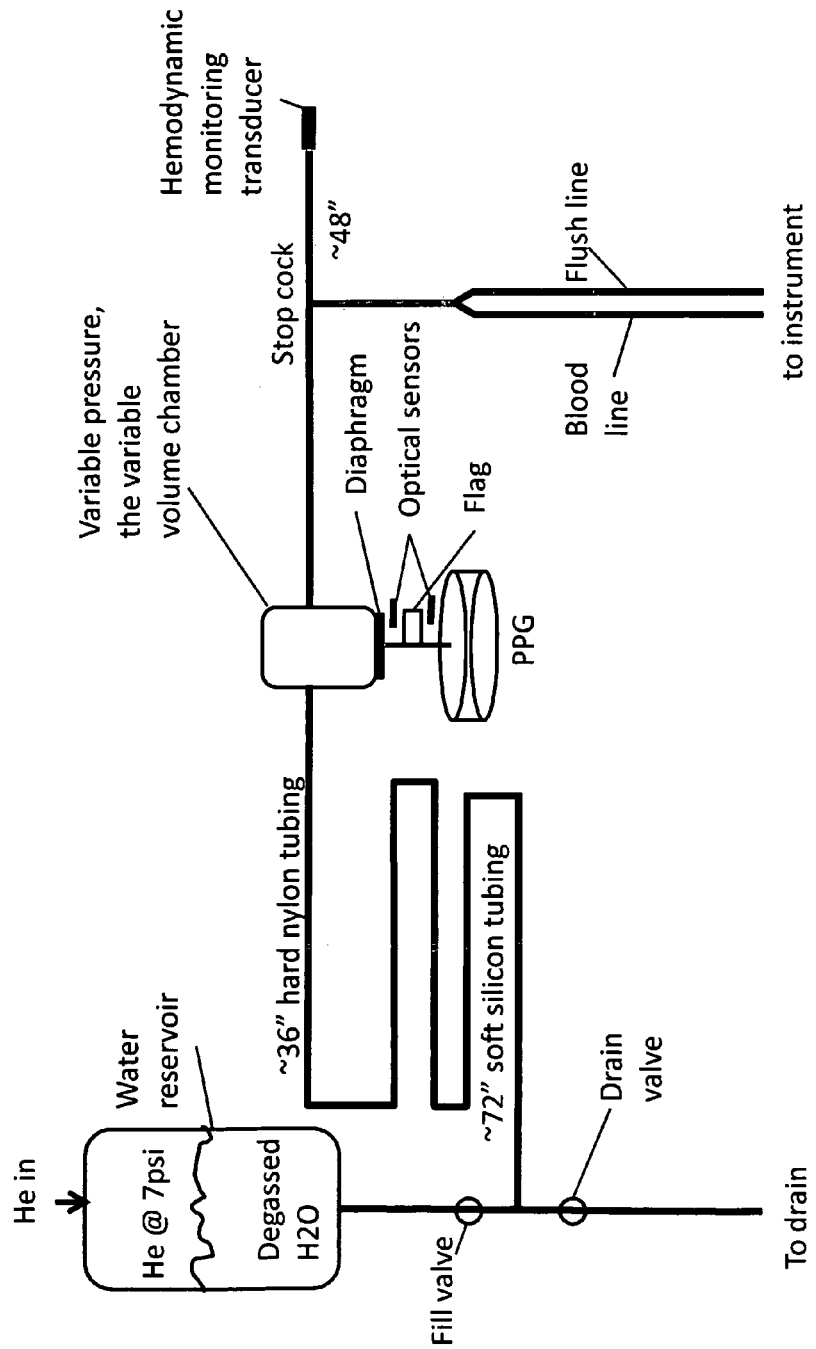
FIG. 10 is a diagram showing a system used to create an artificial patient with a variable pressure, variable volume chamber.
Figure 11:
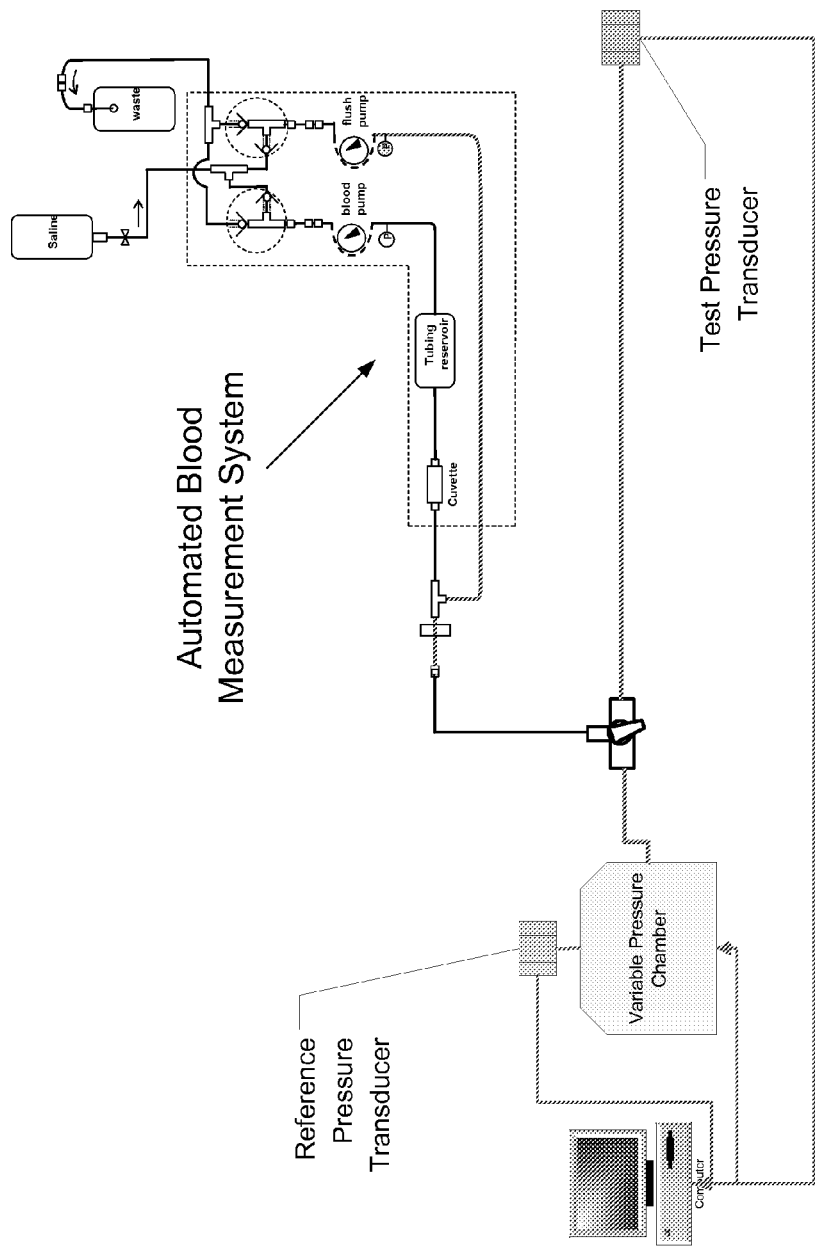
FIG. 11 is a schematic depiction of a test configuration for accessing pressure differences.
Figure 12:
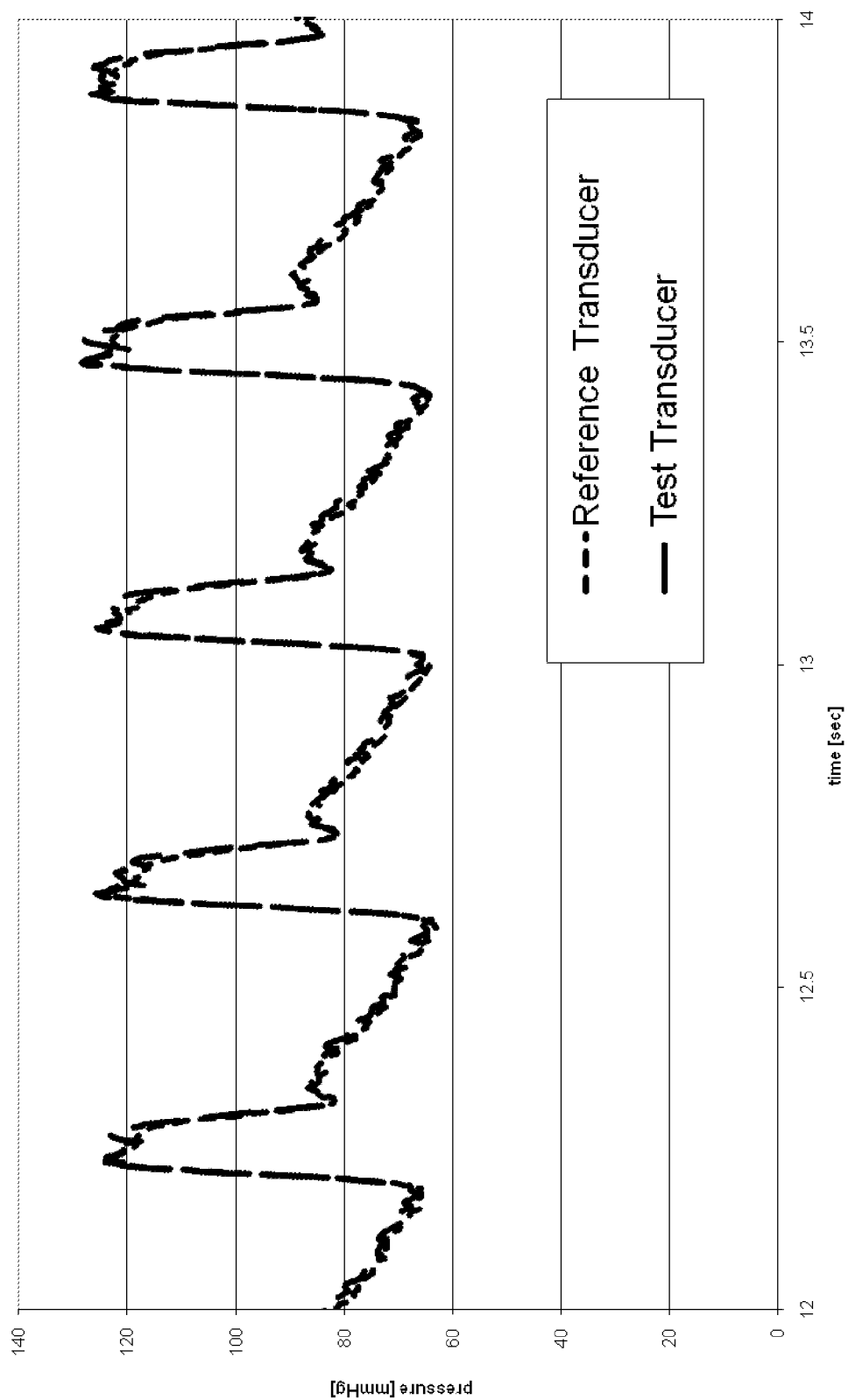
FIG. 12 is an illustration of waveform recordings from both a reference transducer and a test transducer with no bubble present.

Experimental Testing. To quantify potential bubble generation and its impact on hemodynamic monitoring, a study was conducted using a system that could simulate arterial pressure waves. The system comprised a variable pressure, variable volume chamber (serving as an artificial patient) that could create variable pressures that matched an arterial pressure waveform under infusion and withdrawal conditions. The pressure waveforms used were obtained from a physiological database and had heart rates between 60-120 bpm with a pressure range of 150/50 mmHg. Pulse pressure generation was obtained by a diaphragm connected to a voice coil. During infusion or withdrawal, the volume of the chamber was maintained within a reasonable range so that the pressure generation system can create accurate reproductions of arterial pressure waves. A volume control mechanism maintained the volume of the chamber so that the voice coil operated within its normal/linear range. FIG. 10 illustrates the overall system configuration. FIG. 11 shows the relationship between the pressure transducers under test and their relationship to the variable pressure chamber. A reference pressure transducer recorded the pressure generated at the artificial patient while a second test transducer recorded the pressures in a configuration that mirrors a hemodynamic monitoring setup. Comparison between the reference and test readings enabled determination of measurement errors. FIG. 12 shows an illustrative arterial pressure tracing. The agreement between the reference transducer and the test transducer is extremely good. Both pressure recordings are plotted but the level of agreement makes delineation of the two lines difficult.

The impact of multiple measurement cycles on hemodynamic monitoring performance was determined by conducting multiple measurements. The variable pressure, variable volume system (also known as an artificial patient) was attached as shown in FIG. 11. A standard blood measurement cycle was initiated and reference pressure transducer and test pressure transducer measurements recorded. The experimental set-up enables the full characterization of hemodynamic monitoring performance. AAMI document titled "Evaluation of Clinical Systems for Invasive Blood Pressure Monitoring" describes a number of tests that can be used. For characterization of the system, the sweep test was utilized for calculation of the natural frequency and damping values. Additionally, a measurement comparison between the reference and test pressure transducer could be performed.

Figure 13:
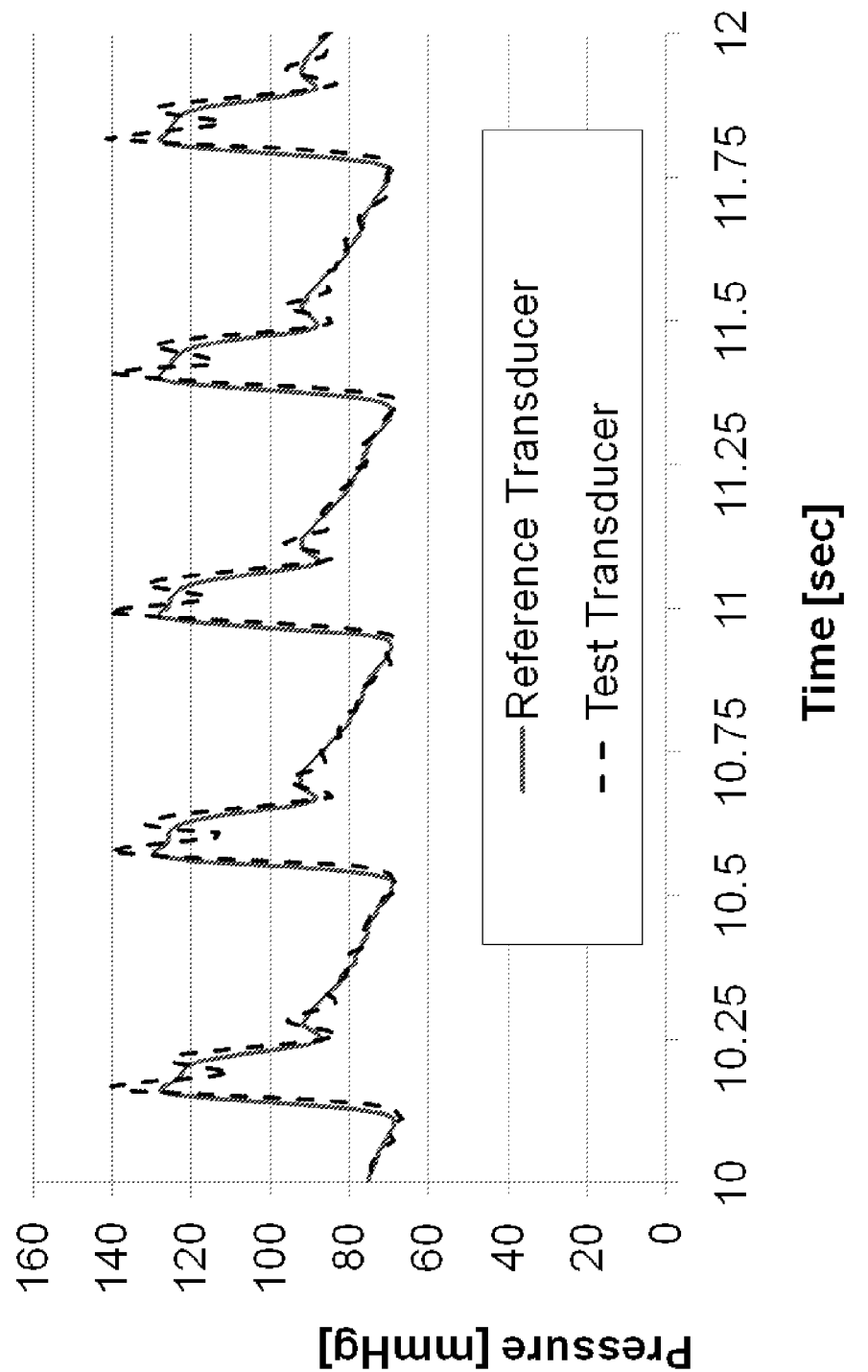
FIG. 13 is an illustration of waveform recordings from both a reference transducer and a test transducer following multiple automated measurements.
Figure 14:
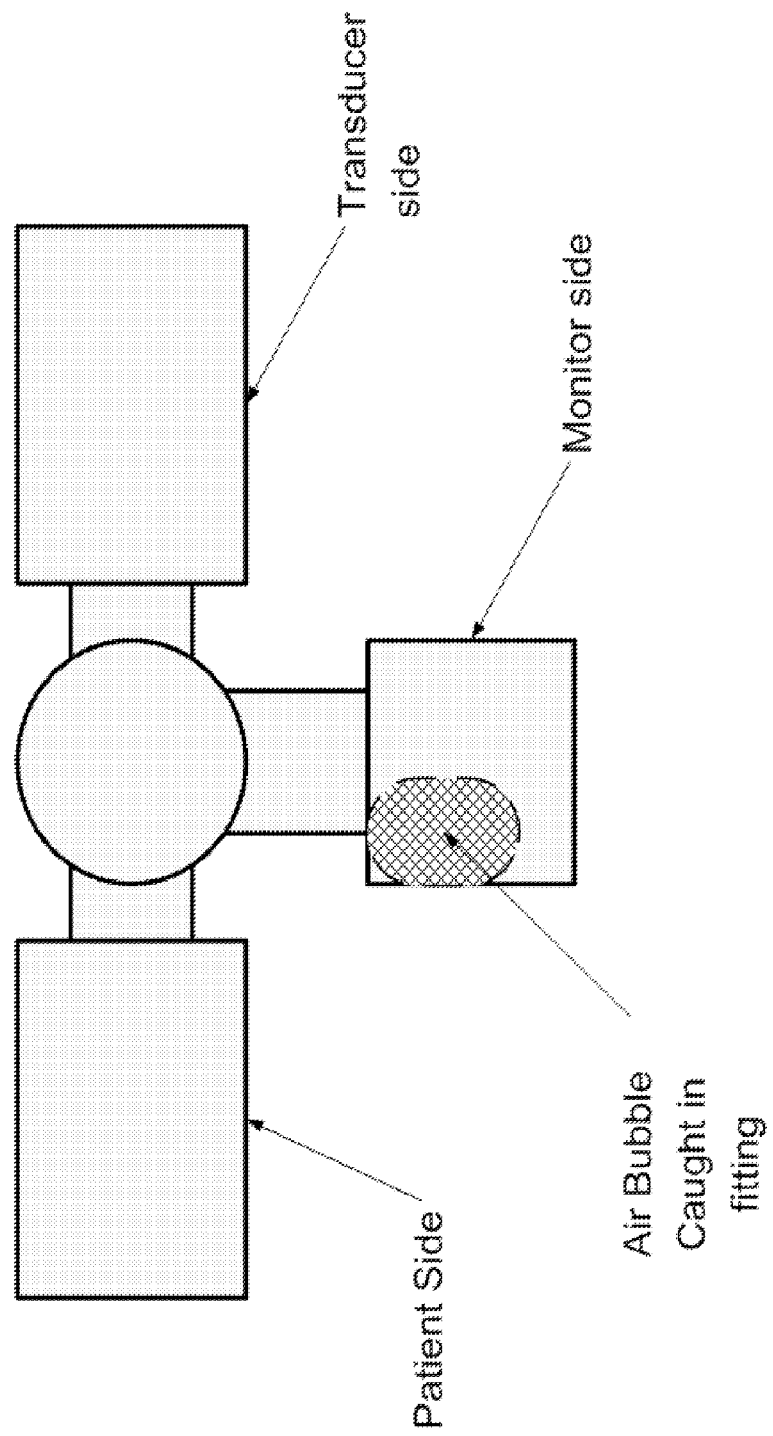
FIG. 14 is an illustration of an air bubble in a stopcock.

The use of multiple measurements demonstrated the generation or presence of bubbles in the tubing following an automated measurement. The bubbles were of sufficient size such that they adversely influenced the accuracy of the pressure measurements. FIG. 12 shows an arterial waveform and the agreement between the reference and test transducers before a measurement. FIG. 13 shows the error between the reference and test transducers after a measurement. Examination of the system revealed the presence of a small bubble in the stopcock on the side towards the automated measurement system. FIG. 14 is an illustration of the bubble location with the bubble size drawn approximately to scale relative to the stopcock.

Figure 15:
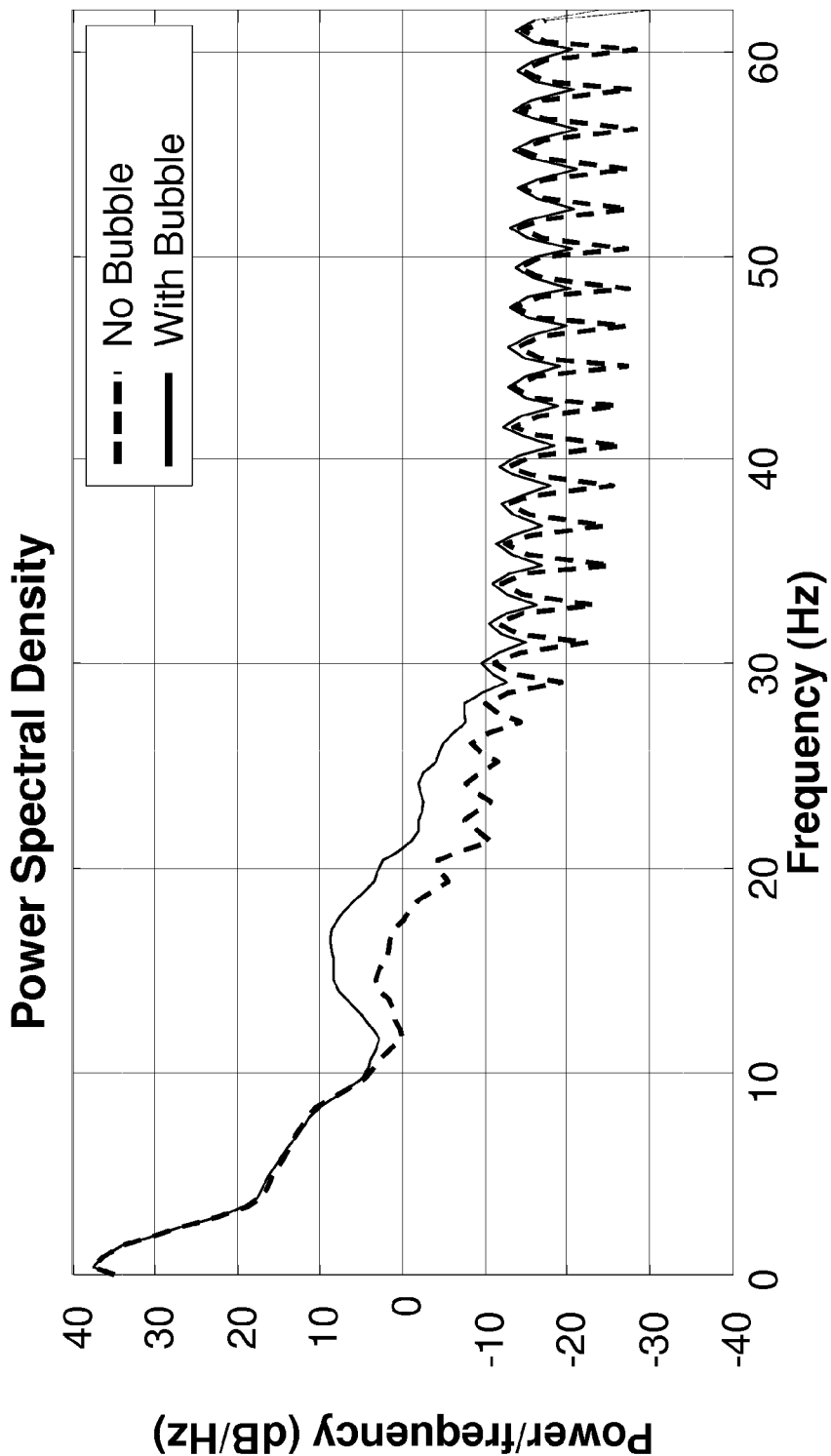
FIG. 15 is an illustration of the spectral power density for waveform recordings pre-measurement and post-measurement.

Examination of FIGS. 12 and 13 shows that frequency content or response of the waveform has been altered by the bubble. For purposes of this application, frequency response or frequency content are used in the broadest of terms to simply imply some assessment of the frequency components of a time varying signal on any difference arising from differences in frequency content of the signal under examination. In classic terms, frequency response is the measure of any system's output spectrum in response to an input signal and is typically characterized by the magnitude of the system's response, measured in decibels (dB), and the phase, measured in radians, versus frequency. For the purpose of comparing two waveforms in this application such a rigorous definition is not applied an in fact an assessment of frequency response could entail a visual inspection such as was conducted when looking at FIGS. 12 and 13. During the period of the blood measurement, the waveform can change in ways consistent with changes in physiology. Therefore the method of comparison should be as insensitive to physiological changes as possible, while being sensitive to the impact of a bubble. Likely physiological changes in the arterial waveform include changes in amplitude, either systolic or diastolic pressure, and changes in heart rate. As heart rates are in the range of 60 to 130 for adults, most changes in heart rate over a limited time of several minutes will comprise changes of less than 10 beats/minute. Thus, the heart rate will appear as a frequency in the 1 to 2 hertz range. A comparison process well suited to identifying the impact of a bubble in the presence of a physiological change is the power spectral density function. The power spectral density (PSD) is a positive real function of a frequency variable associated with a stationary stochastic process, or a deterministic function of time, which has dimensions of power per Hz, or energy per Hz. It is often called simply the spectrum of the signal. Intuitively, the spectral density captures the frequency content of a stochastic process and helps identify periodicities. The power spectral density (PSD) describes how the power of a signal or time series is distributed with frequency. As a PSD is used to examine the frequency content of a given time series, a comparison of PSDs is well suited to detect the presence of new frequencies in a given time series. Changes in heart rate will cause changes in the lower frequencies where a bubble will introduce additional frequencies in the 10 Hz range. The PSD for both the pre-measurement and post measurement waveforms was determined. FIG. 15 is an illustration of the resulting PSDs. As can be easily seen the solid line (bubble present) has significantly more power in the range between 10 and 30 Hz. An increase of this nature can be indicative of a bubble and the nurse can be alerted to check for potential bubbles or the system can automatically clear the bubble.

As one of skill in the art will recognize a number of comparison methods are well suited to examining the differences in spectral content between two time sequences.

Figure 16:
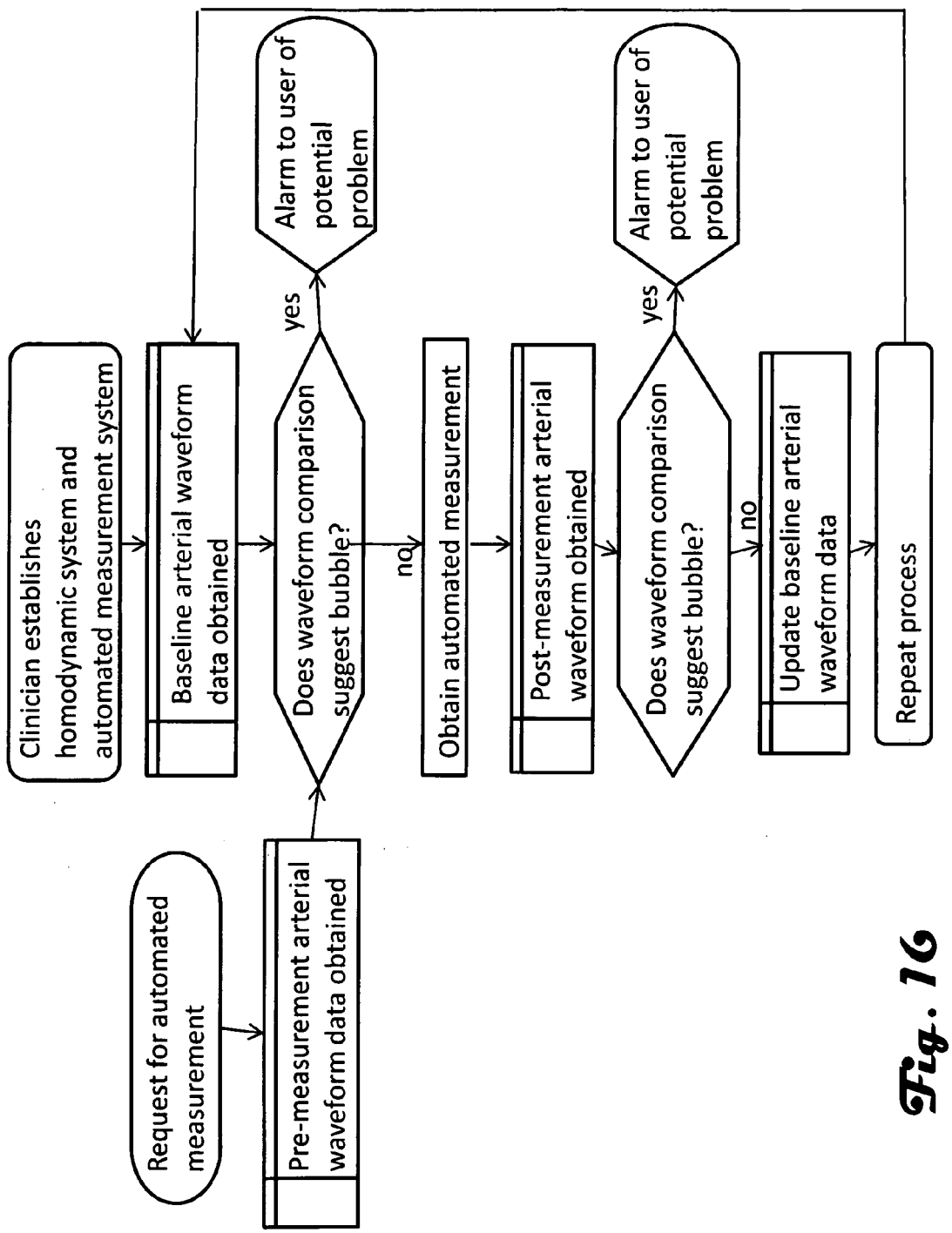
FIG. 16 is a flowchart depicting an example comparison sequence that can be used in clinical practice.

FIG. 16 shows an example flowchart of a process that can be suitable. As mentioned above there is an initial set-up to establish correct operation of the hemodynamic system, for example by visual inspection by a clinician, or for example by the fast flush test, or for example by a combination of those or other methods apparent to those skilled in the art. Data at this point in time can be saved for future reference and can establish a baseline of performance. At some point in time the system seeks to take an automated measurement. To re-establish a baseline arterial waveform the system can procure a second waveform and compare it to the original baseline waveform. If the comparison indicates likelihood of a bubble, then the clinician can be alerted, or the system can automatically manage the bubble if possible. In some circumstances, the quality of the comparison can be improved if the pre-measurement waveform and the post measurement waveform are determined without a large elapsed time between determinations. Assuming there is no evidence of a bubble then an automated measurement can be made. Following completion of the automated measurement a post-measurement waveform can be procured and a comparison with the pre-measurement waveform conducted. If there is evidence of a bubble the clinician can be alerted or the system can automatically manage the bubble, if possible, prior to re-initiation of hemodynamic monitoring. Assuming no evidence of bubbles, the baseline data to be used for future comparisons can be updated. Updating the baseline waveform data can allow changes in the system that are not due to bubbles, e.g., aging of tubing or other components, or component property changes due to temperature changes, to be accommodated without contributing to erroneous bubble indications.

Figure 17:
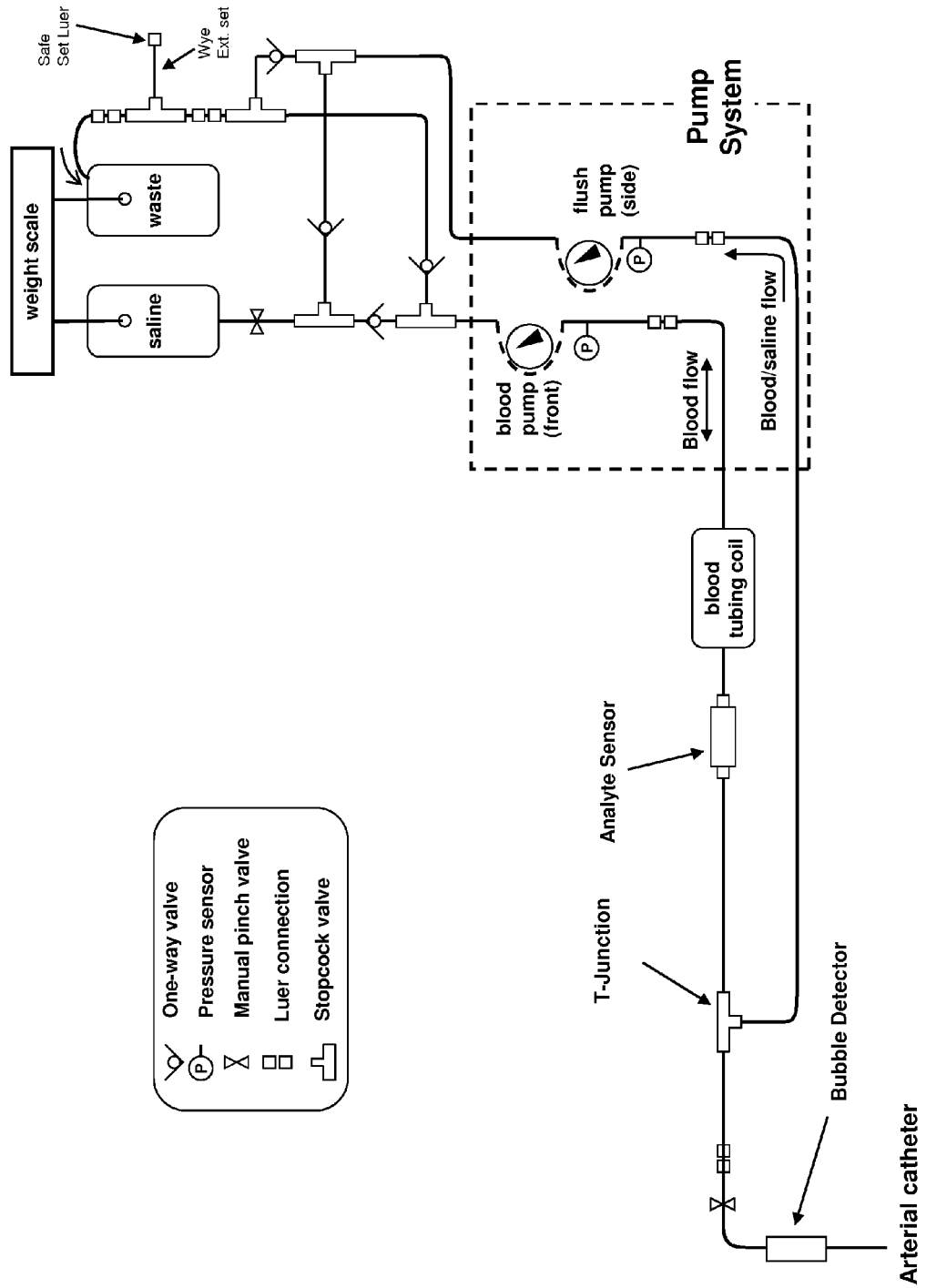
FIG. 17 is a schematic depiction of an example embodiment of an automated blood analyte measurement system.

FIG. 17 is an example of an automated blood analyte measurement system. This system has a second tubing loop and pressure transducer that enables the effective removal of bubbles to waste. In practice, the blood for measurement is pulled to the analyte sensor and a measurement made with subsequent re-infusion into the patient. Several steps associated with cleaning the system can be performed after the measurement sequence. If a bubble is detected the system has the ability to move the bubble into the waste bag. An example process such as the following can be used. The blood pump can push fluid toward the patient while the flush pump pulls fluid away from the patient thus moving a bubble located between the pumps and the T-junction to a waste channel such as a waste bag as shown in the figure. By operating the pumps at the same rate but in opposite directions, the bubble can be moved to waste without risk of infusing the bubble into the patient. After an appropriate volume has been pumped the system can conduct a waveform comparison like those described elsewhere herein. If there is still evidence of a bubble then the likely location of the bubble is in the tubing between the bubble detector and the T-junction. To remove this bubble, the system can withdraw fluid toward and past the T-junction such that any bubble originally in the tubing between the T-junction and the patient is now located in the tubing sections between the t-junction and the pumps. Following the withdrawal process, the pumps can be activated in the manner described above so that the bubble is moved to the waste bag. To ensure that the system is now ready to begin hemodynamic monitoring, a final waveform test can be conducted. If such a test continued to indicate evidence of a bubble then the process can be repeated or an alarm initiated such that clinician resolution of the situation was initiated.

Figure 18:
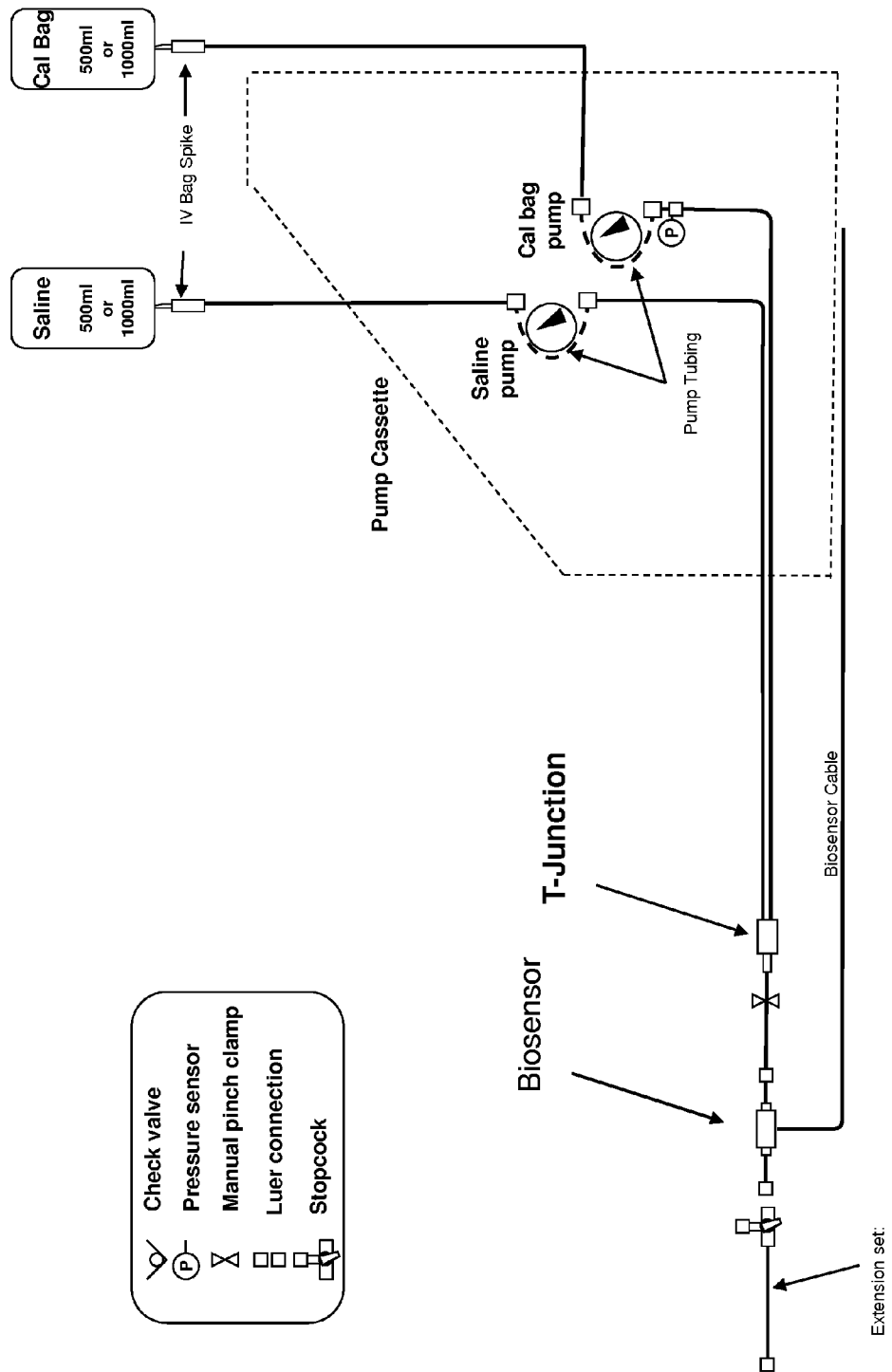
FIG. 18 is a schematic depiction of an example embodiment of an automated blood analyte measurement system.

FIG. 18 shows another example embodiment of a blood access system but where the sensor is located close to the patient. As shown the blood access system has only one pressure transducer but others can be added as appropriate for the desired operation. The same general concepts to bubble detection and subsequent management can be applied as described above.

Figure 19:
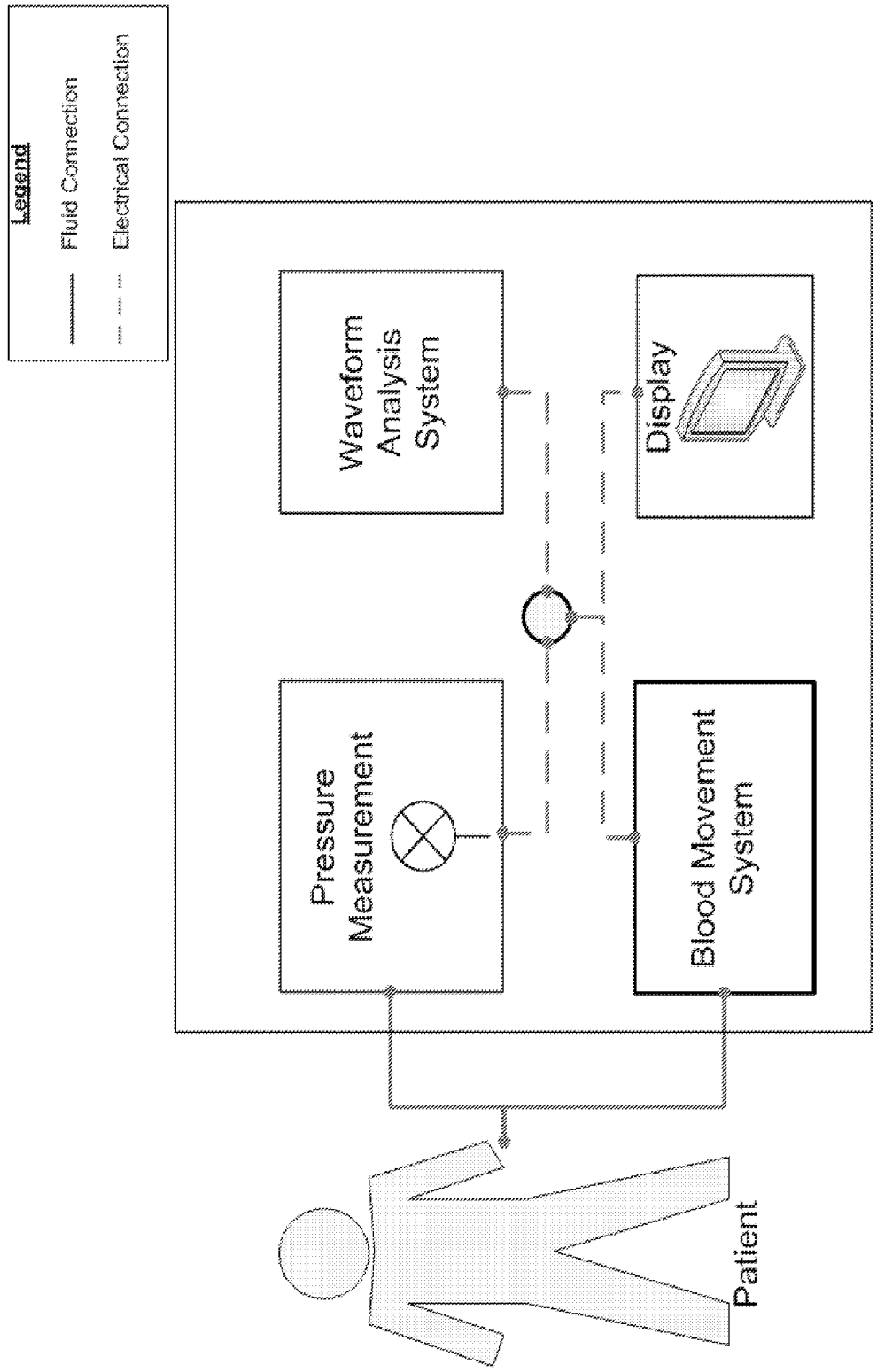
FIG. 19 is a block diagram depicting the system contained in a single box.
Figure 20:
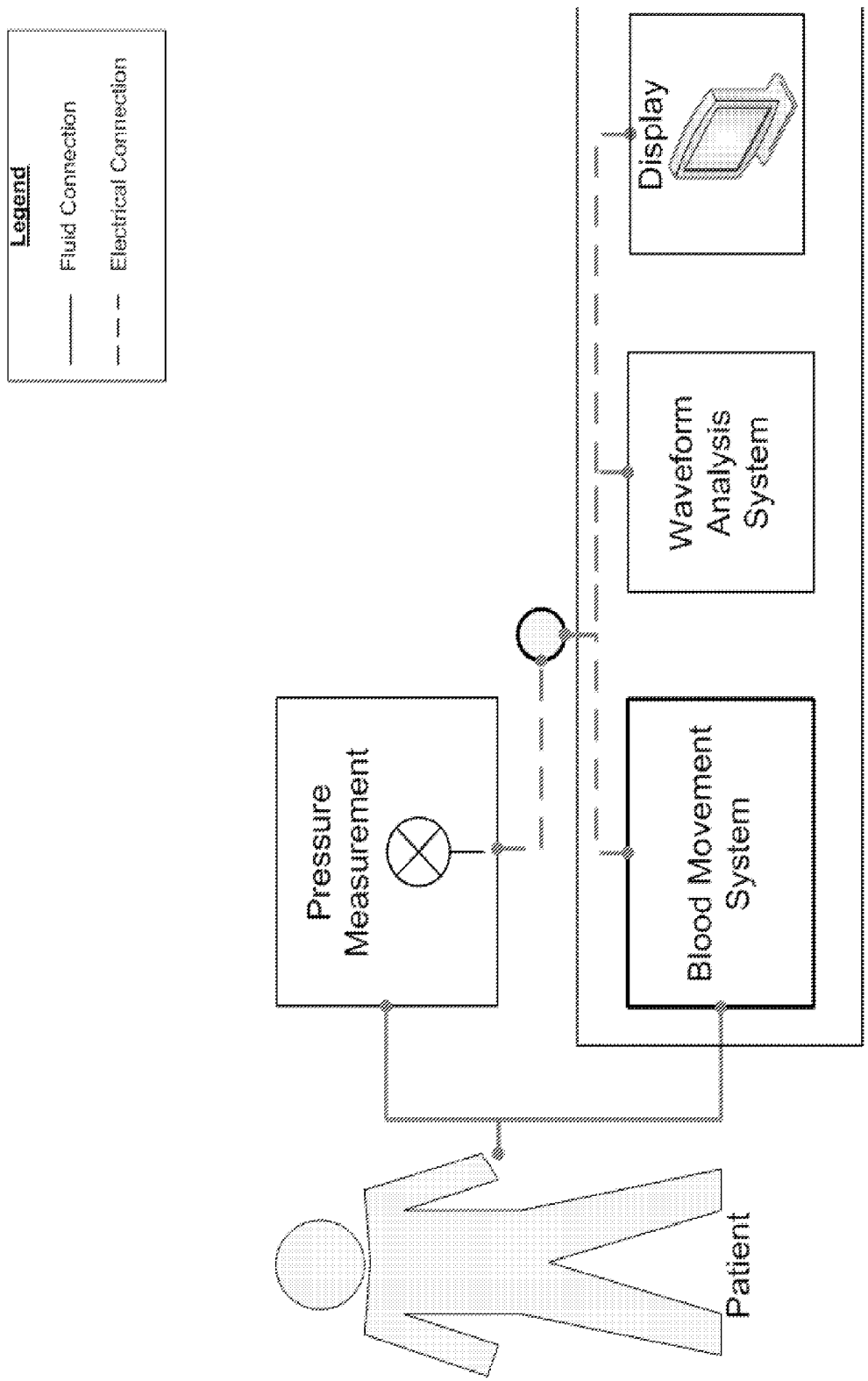
FIG. 20 is a block diagram depicting the pressure measurement system as a separate entity in communication with other systems.
Figure 21:
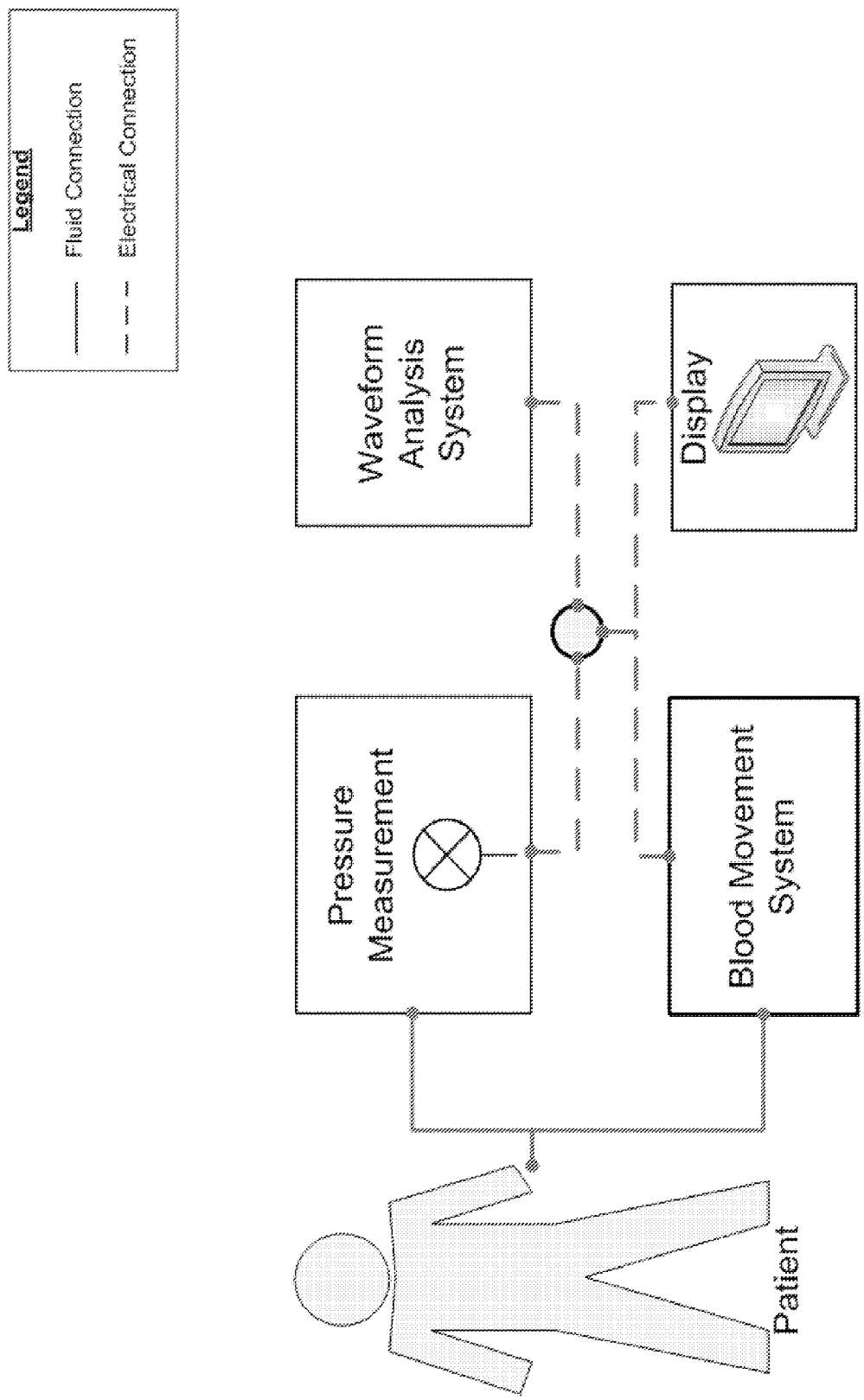
FIG. 21 is a block diagram depicting that all systems could be physically distinct with only information transfer between the sub-systems.

In implementation, the blood access system and the pressure measurement system must be able to exchange information. In general terms the integrated system is composed of four basic parts: (1) Blood movement system (2) pressure measurement system, (3) waveform analysis system and (4) display system. The various systems must be able to exchange information for the effective implementation of the bubble detection methodology. As shown in FIG. 19 these system can be contained in a single box. The communication shown is illustrated as an electrical connection but any form of communication would work to include wireless communication. FIG. 20 shows the pressure measurement system as a separate entity in communication with the other systems. In such a scenario a conventional pressure transducer could provide waveform information to the automated blood analyte measurement system that contains the blood movement system, waveform analysis system and a display. In a final embodiment, FIG. 21, all systems could be physically distinct with only information transfer between the sub-systems.

The present invention has been described as set forth herein. It will be understood that the above description is merely illustrative of the applications of the principles of the present invention, the scope of which is to be determined by the claims viewed in light of the specification. Other variants and modifications of the invention will be apparent to those of skill in the art.

I claim:
1. A method of determining the presence of a bubble in a blood access system comprising at least one pressure detector, comprising:
   a. Using the pressure detector to determine a first frequency response of the system at a first time;
   b. Using the pressure detector to determine a second frequency response of the system at a second time;
   c. Determining if a bubble is present in the system by comparing the first and second frequency responses.
2. A method as in claim 1, wherein the blood access system is in fluid communication with the circulatory system of a patient.

3. A method as in claim 2, wherein
   a. determining a first frequency response comprises determining a frequency-dependent characteristic of the output of the pressure detector responsive to changes in blood pressure in the circulatory system, and
   b. determining a second frequency response comprises determining a frequency-dependent characteristic of the output of the pressure detector responsive to changes in blood pressure in the circulatory system.

4. A method as in claim 1, wherein comparing the first and second frequency responses comprises subtraction, division, Fourier transform analysis, wavelet analysis, vector comparison, derivative processing, or a combination thereof.

5. A method as in claim 1, wherein
   a. determining a first frequency response comprises determining the power spectral density of the output of the pressure detector during a first time interval, and
   b. determining a second frequency response comprises determining the power spectral density of the output of the pressure detector during a second time interval, and
   c. determining if a bubble is present comprises determining whether the second frequency response indicates more power at frequencies corresponding to presence of a bubble than does the first frequency response.

6. A method of determining the presence, concentration, or both of an analyte in the blood of a patient, comprising:
   a. Placing a blood access system in fluid communication with the circulatory patient, wherein the blood access system comprises at least one pressure sensor, at least one analye sensor, and at least one pump;
   b. Using the pressure sensor to determine the frequency response of the blood access system at a first time before step c;
   c. Operating the pump to withdraw blood from the patient to the analyte sensor;
   d. Operating the analyte sensor to determine the presence, concentration, or both of an analyte in the withdrawn blood;
   e. Using the pressure sensor to determine the frequency response of the blood access system at a second time after step c;
   f. Determining if a bubble is present in the blood access system by comparing the frequency response determined at the first time with the frequency response determined at the second time.

7. A method as in claim 6, further comprising operating the pump to move the bubble out of portions of the blood access system where the bubble has an effect on the frequency response of the blood access system.

8. A method as in claim 6, further comprising initiating an alert signal indicating the presence of a bubble if a bubble is determined to be present.

9. A method as in claim 6, wherein comparing the frequency response determined at the first time with the frequency response determined at the second time comprises subtraction, division, Fourier transform analysis, wavelet analysis, vector comparison, derivative processing, or a combination thereof, of the frequency responses.

10. A method as in claim 6, wherein
    a. Step b comprises determining the power spectral density of the output of the pressure detector during a first time interval, and
    b. Step e comprises determining the power spectral density of the output of the pressure detector during a second time interval, and
    c. Step f comprises determining whether the frequency response from step e indicates more power at frequencies corresponding to presence of a bubble than does the frequency response from step b.

11. A method of detecting bubbles in a hemodynamic monitoring system, comprising:
    a. Determining a frequency response of the system;
    b. Determining if a bubble is present in the system by comparing the frequency response determined in step a with a baseline frequency response, wherein the baseline frequency response is either (a) a frequency response of the system determined at an earlier time when the system was determined to be free of bubbles, or (b) a combination of frequency responses determined at a plurality of earlier times when the system was determined to be free of bubbles.

12. A method as in claim 11, wherein comparing the frequency response determined in step a with a baseline frequency response comprises subtraction, division, Fourier transform analysis, wavelet analysis, vector comparison, derivative processing, or a combination thereof, of the frequency responses.

13. A method as in claim 11, further comprising initiating an alert signal indicating the presence of a bubble if a bubble is determined to be present.

14. A method as in claim 11, wherein comparing the frequency response determined in step a with a baseline frequency response comprises determining if the frequency response determined in step a indicates more power in frequencies corresponding to presence of a bubble than does the baseline frequency response.

15. An apparatus for the measurement of an analyte in the circulatory system of a patient, comprising:
    a. A patient interface element, adapted to be placed in fluid communication with the circulatory system of a patient;
    b. An analyte sensor, mounted in fluid communication with the patient interface element;
    c. A pressure sensor, mounted in fluid communication with the patient interface element;
    d. A pumping subsystem, mounted in fluid communication with the analyte sensor and with the patient interface element;
    e. A control subsystem, responsive to the pressure sensor and controlling the pumping subsystem, wherein the control subsystem operates the pump to draw blood from the circulatory system to the analyte sensor, and wherein the control subsystem implements the method of claim 11 after each such draw.

* * * * *